(12) United States Patent
Mach et al.

(10) Patent No.: US 9,410,210 B2
(45) Date of Patent: *Aug. 9, 2016

(54) FILTRATION METHODS AND DEVICES

(76) Inventors: Patrick A. Mach, Shorewood, MN (US); Raj Rajagopal, Woodbury, MN (US); Wensheng Xia, Woodbury, MN (US); Jinsheng Zhou, Woodbury, MN (US); Chunmei Guo, Woodbury, MN (US); Guoping Mao, legal representative, Woodbury, MN (US)

( * ) Notice: Subject to any disclaimer, the term of this patent is extended or adjusted under 35 U.S.C. 154(b) by 392 days.

This patent is subject to a terminal disclaimer.

(21) Appl. No.: 13/701,935

(22) PCT Filed: Jun. 6, 2011

(86) PCT No.: PCT/US2011/039242
§ 371 (c)(1),
(2), (4) Date: Apr. 26, 2013

(87) PCT Pub. No.: WO2011/156258
PCT Pub. Date: Dec. 15, 2011

(65) Prior Publication Data
US 2013/0344488 A1  Dec. 26, 2013

Related U.S. Application Data

(60) Provisional application No. 61/352,205, filed on Jun. 7, 2010.

(51) Int. Cl.
| *C12Q 1/68* | (2006.01) |
| *C12Q 1/04* | (2006.01) |
| *G01N 33/68* | (2006.01) |
| *B01D 63/00* | (2006.01) |
| *C12Q 1/24* | (2006.01) |

(52) U.S. Cl.
CPC ............... *C12Q 1/689* (2013.01); *B01D 63/00* (2013.01); *C12Q 1/04* (2013.01); *C12Q 1/24* (2013.01); *G01N 33/68* (2013.01); *B01D 2323/39* (2013.01)

(58) Field of Classification Search
USPC .............................. 435/34, 6.12, 7.1; 210/321
See application file for complete search history.

(56) References Cited

U.S. PATENT DOCUMENTS

| 3,342,328 | A | 9/1967 | Swenson |
| 4,539,256 | A | 9/1985 | Shipman |
| 4,726,989 | A | 2/1988 | Mrozinski |
| 4,867,881 | A | 9/1989 | Kinzer |
| 4,920,105 | A | 4/1990 | Zelman |
| 5,120,594 | A | 6/1992 | Mrozinski |
| 5,242,595 | A | * | 9/1993 | Morgart et al. ............... 210/636 |
| 5,260,360 | A | 11/1993 | Mrozinski et al. |
| 5,443,727 | A | 8/1995 | Gagnon |
| 5,506,279 | A | 4/1996 | Babu et al. |
| 5,766,868 | A | 6/1998 | Seto |
| 5,770,086 | A | 6/1998 | Indriksons et al. |
| 5,993,954 | A | 11/1999 | Radovanovic et al. |
| 6,096,213 | A | 8/2000 | Radovanovic et al. |
| 6,106,483 | A | 8/2000 | Guirguis |
| 6,171,689 | B1 | 1/2001 | Kaytor et al. |
| 6,461,724 | B1 | 10/2002 | Radovanovic et al. |
| 6,517,709 | B1 | 2/2003 | Cardwell et al. |
| 6,669,981 | B2 | 12/2003 | Parsons et al. |
| 6,861,067 | B2 | 3/2005 | McGhee et al. |
| 7,140,496 | B2 | 11/2006 | Nagoya et al. |
| 7,993,523 | B2 * | 8/2011 | Chen .................. B01D 39/1623 210/321.6 |
| 2003/0217965 | A1 | 11/2003 | Kools |
| 2004/0063169 | A1 * | 4/2004 | Kane ....................... C12Q 1/24 435/30 |
| 2004/0157971 | A1 | 8/2004 | Kim |
| 2005/0067343 | A1 | 3/2005 | Zulauf et al. |
| 2005/0244943 | A1 * | 11/2005 | Ladisch ................... C12Q 1/24 435/252.3 |
| 2006/0062854 | A1 | 3/2006 | Chandra et al. |
| 2007/0111194 | A1 | 5/2007 | Pellaux et al. |

FOREIGN PATENT DOCUMENTS

| CN | 1800038 | 7/2006 |
| JP | 56-158144 | 12/1981 |
| KR | 10-2004-0040692 | 5/2004 |
| WO | WO 2006/069307 | 6/2006 |
| WO | WO 2007/146722 | 12/2007 |
| WO | WO 2010/071764 | 6/2010 |
| WO | WO 2010/078234 | 7/2010 |
| WO | WO 2011/152967 | 12/2011 |
| WO | WO 2011/153085 | 12/2011 |
| WO | WO 2011/156251 | 12/2011 |

OTHER PUBLICATIONS

Lenntech. Bubble Point. Downloaded from the Lenntech website on Jul. 23, 2014: <http://www.lenntech.com/library/fine/bubble/bubble-point.htm>.*
Field, R.W. et al. Critical Flux Concept for Microfiltration Fouling. Journal of Membrane Science 100 (1995). Elsevier. pp. 259-272.*

* cited by examiner

Primary Examiner — Kagnew H Gebreyesus
Assistant Examiner — Nghi Nguyen

(57) ABSTRACT

A method of filtering a liquid sample that includes passing a sample comprising at least one biological organism through a filter membrane at a passive water volume flux of at least 10 $L/m^2 \cdot h \cdot psi$, wherein the filter membrane comprises a Bubble Point pore size of no more than 1.0 µm, thereby retaining at least one biological organism on the surface of the membrane; and detecting the at least one biological organism retained on the surface of the filter membrane.

24 Claims, 6 Drawing Sheets

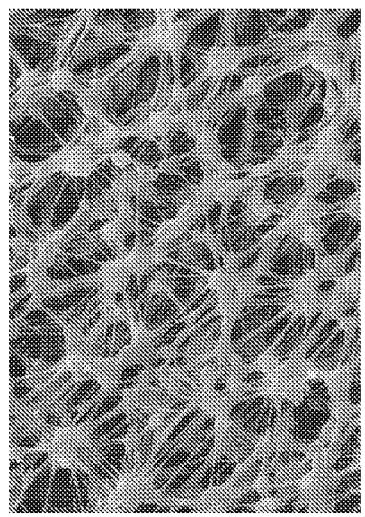
*FIG. 1A* 1μm
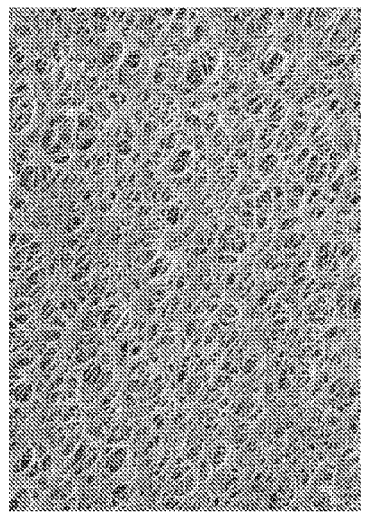
*FIG. 1B* 1μm
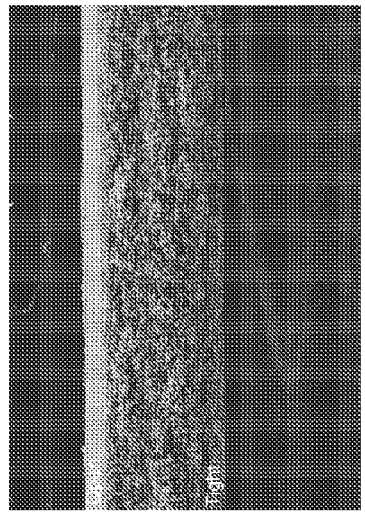
*FIG. 1C* 1μm
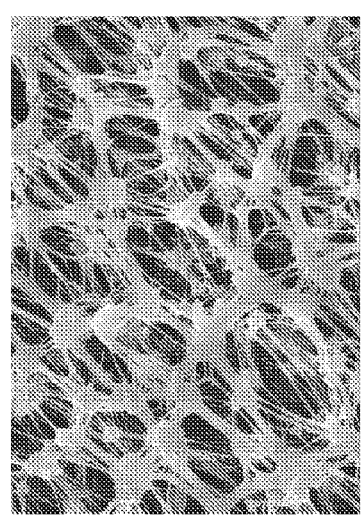
*FIG. 2A* 1μm
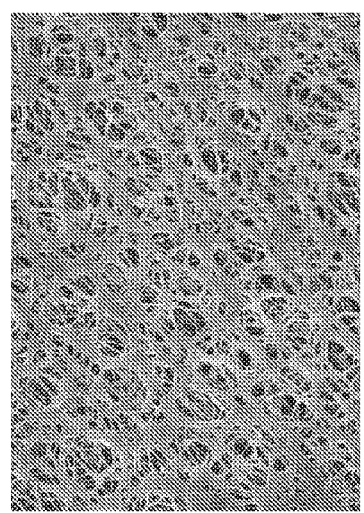
*FIG. 2B* 1μm
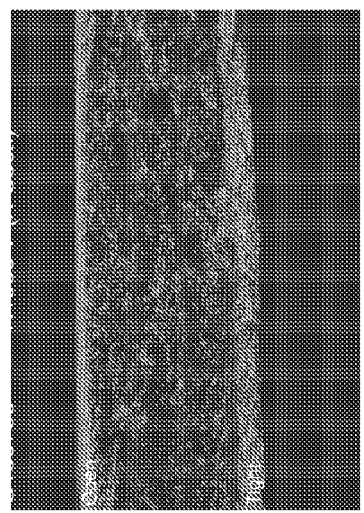
*FIG. 2C* 1μm

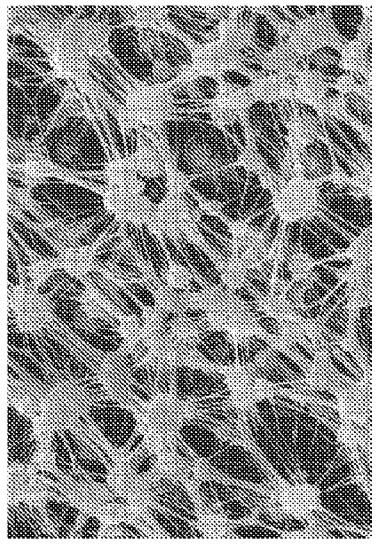 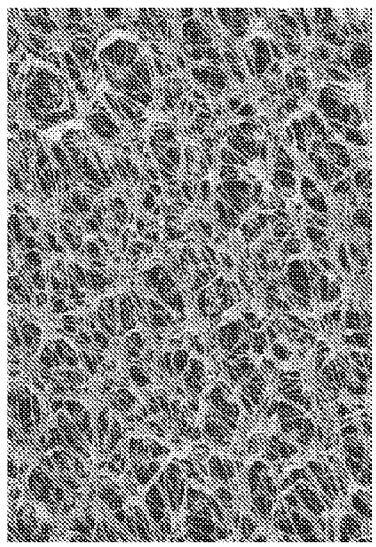 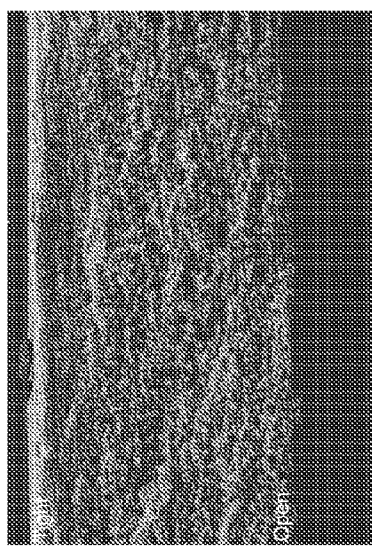
FIG. 3A  FIG. 3B  FIG. 3C
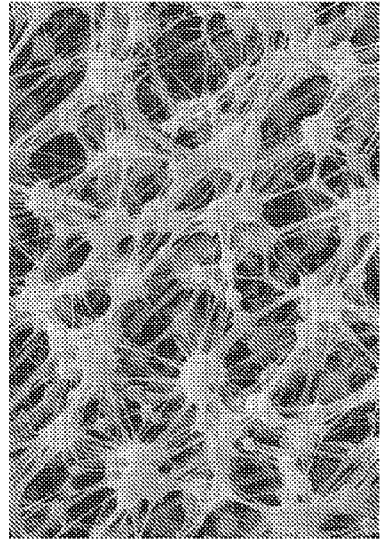 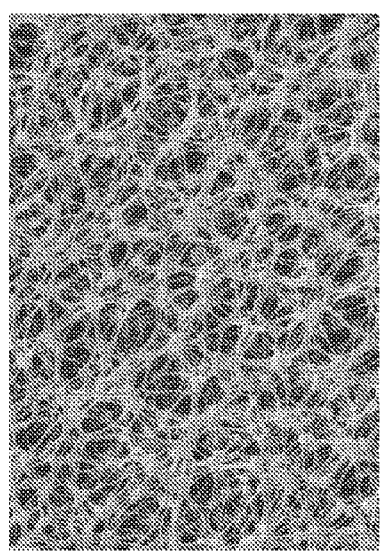 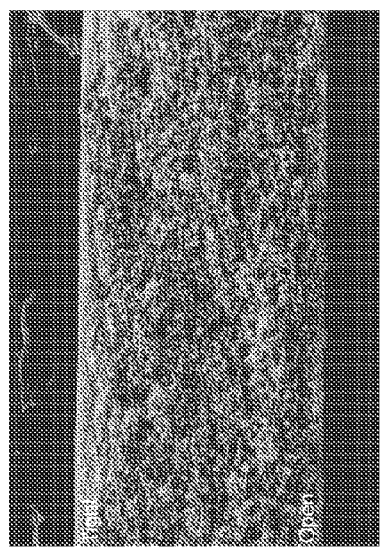
FIG. 4A  FIG. 4B  FIG. 4C

SEQUENCE LISTING

```
<160> NUMBER OF SEQ ID NOS: 6

<210> SEQ ID NO 1
<211> LENGTH: 22
<212> TYPE: DNA
<213> ORGANISM: artificial
<220> FEATURE:
<223> OTHER INFORMATION: oligonucleotide primer

<400> SEQUENCE: 1
tctactttac tggctttggt cg                                             22

<210> SEQ ID NO 2
<211> LENGTH: 21
<212> TYPE: DNA
<213> ORGANISM: artificial
<220> FEATURE:
<223> OTHER INFORMATION: oligonucleotide primer

<400> SEQUENCE: 2
cgtaagggta atgcgaggta c                                              21

<210> SEQ ID NO 3
<211> LENGTH: 26
<212> TYPE: DNA
<213> ORGANISM: artificial
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: conjugated to 6FAM fluorescent label
<220> FEATURE:
<221> NAME/KEY: misc_feature
<222> LOCATION: (26)..(26)
<223> OTHER INFORMATION: conjugated to Iowa Black FQ fluorescent
      quencher

<400> SEQUENCE: 3
aggattcgat aacgtgctga tggtgc                                         26

<210> SEQ ID NO 4
<211> LENGTH: 21
<212> TYPE: DNA
<213> ORGANISM: artificial
<220> FEATURE:
<223> OTHER INFORMATION: oligonucleotide primer

<400> SEQUENCE: 4
```

-continued

```
tcaccatcaa cacttctcac g                                              21

<210> SEQ ID NO 5
<211> LENGTH: 19
<212> TYPE: DNA
<213> ORGANISM: artificial
<220> FEATURE:
<223> OTHER INFORMATION: oligonucleotide primer

<400> SEQUENCE: 5
cagcaactac caggatcgc                                                 19

<210> SEQ ID NO 6
<211> LENGTH: 21
<212> TYPE: DNA
<213> ORGANISM: artificial
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: conjugated to 6FAM fluorescent label
<220> FEATURE:
<221> NAME/KEY: misc_feature
<222> LOCATION: (21)..(21)
<223> OTHER INFORMATION: conjugated to Iowa Black FQ fluorescent
      quencher

<400> SEQUENCE: 6
tgaatacgac accccgaccc g                                              21
```

FILTRATION METHODS AND DEVICES

CROSS REFERENCE TO RELATED APPLICATIONS

This application claims the benefit of U.S. Provisional Patent Application No. 61/352,205, filed Jun. 7, 2010, which is incorporated herein by reference in its entirety.

This application has associated with it a sequence listing with the file name Sequence_Listing 66415US004, created Aug. 21, 2013 and contains 1,774 bytes, which is incorporated herein by reference.

BACKGROUND

Membrane filtration is a standard step in many methods of analyzing a liquid sample for the presence of biological organisms. Such analyses are commonly performed in the interest of, for example, food safety, water quality, and/or environmental monitoring and/or study. Many membranes having an average pore size of 0.45 μm or less (e.g., cellulose acetate, nylon, etc. membranes) may be able to trap bacteria and allow growth of the trapped bacteria when placed on a suitable medium. It can be difficult, however, to recover bacteria from such membranes. These membranes, despite having an average pore size of 0.45 μm or less, typically possess a significant number of pores at the membrane surface that are larger than the biological organisms and, therefore, have torturous pore structure into which biological organisms may become trapped.

SUMMARY OF THE INVENTION

In one aspect, the present invention provides a method of filtering a liquid sample. Generally, the method includes passing a sample comprising at least one biological organism through a filter membrane at a passive water volume flux of at least 10 L/m$^2$·h·psi, wherein the filter membrane comprises a Bubble Point pore size of no more than 1.0 μm, thereby retaining at least one biological organism on the surface of the membrane; and detecting the at least one biological organism retained on the surface of the filter membrane.

In certain embodiments, the biological organism may be detected in situ on the filter membrane, while in other embodiments, the biological organism may be removed from the filter membrane before being detected. Thus, in some embodiments, the method includes eluting retained biological organisms from the filter membrane.

In some embodiments, the method can further include quantifying at least one of the biological organisms.

In some embodiments, the method can include detecting and/or quantifying the biological organism no more than 24 hours after the sample is passed through the filter membrane.

In some embodiments, the liquid sample can include, for example, food samples, environmental samples, or water samples.

In some embodiments, the filter membrane may be provided in functional communication with an absorbent member.

In some embodiments, the method can include reducing the volume of the liquid sample by at least 50%.

In another aspect, the present invention provides a filter device. Generally, the filter device includes a pocket comprising a pocket surface that defines a pocket volume; an absorbent member disposed on at least a portion of the pocket surface; and a filter membrane disposed on at least a portion of the absorbent member in fluid communication with the pocket volume.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. SEM image of R1933-18 (nascent, 0.23 μm) membrane. 1A Open side (5000×), 1B Tight side (5000×), 1C Cross-section (500×).

FIG. 2. SEM image of R1933-7 (nascent, 0.34 μm) membrane. 2A Open side (5000×), 2B Tight side (5000×), 2C Cross-section (500×).

FIG. 3. SEM image of R1933-8B (nascent, 0.51 μm) membrane. 3A Open side (5000×), 3B Tight side (5000×), 3C Cross-section (500×).

FIG. 4. SEM image of R1901-11 (nascent, 0.74 μm) membrane. 4A Open side (5000×), 4B Tight side (5000×), 4C Cross-section (500×).

DETAILED DESCRIPTION OF ILLUSTRATIVE EMBODIMENTS

Figure 5A:
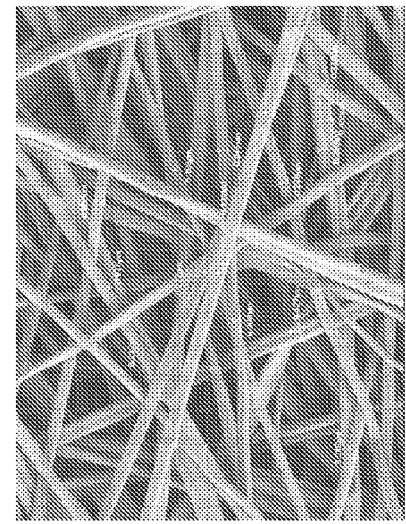
FIG. 5. SEM image of PAN membranes (10,000×). 5A PAN-1 (0.613 μm), 5B PAN-2 (0.531 μm), 5C PAN-3 (0.367 μm).
Figure 5B:
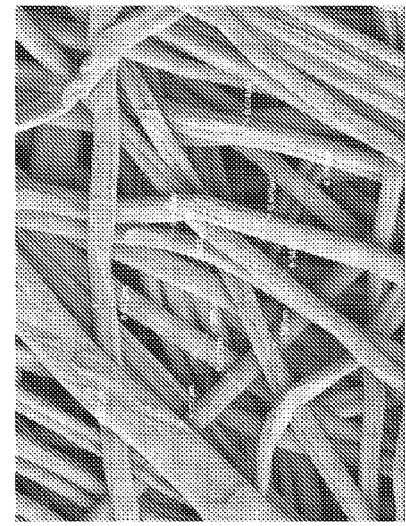
Figure 5C:
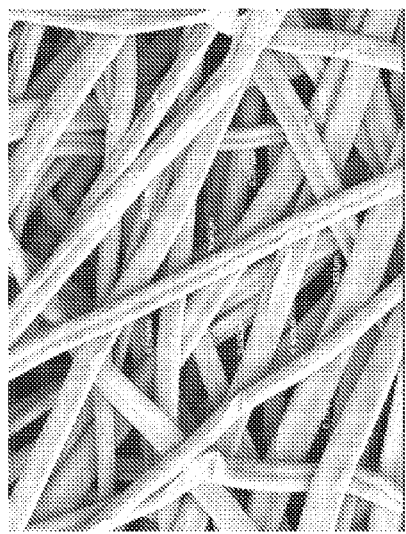
Figure 6A:
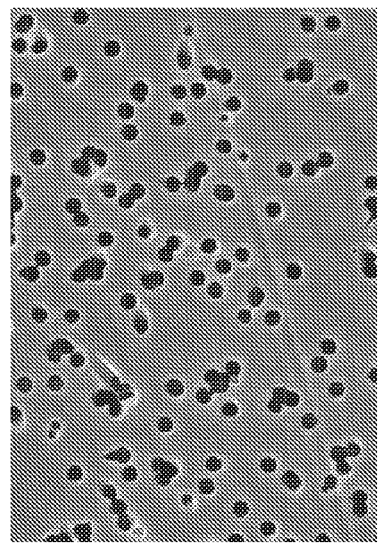
FIG. 6. SEM images (10,000×) of MF-Millipore Type HAWP (0.4 μm) (6A) and Isopore polycarbonate filter (0.4 μm) (6B). Both membrane images are of sides receiving sample.
Figure 6B:
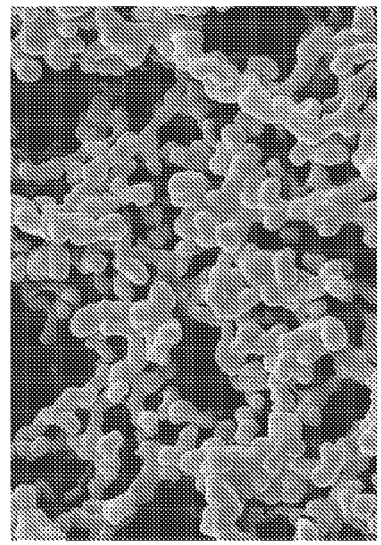

We describe herein methods in which liquid samples may be analyzed for the presence of one or more biological organisms. Depending upon the specific context in which the methods are practiced, the methods can involve passing a liquid sample through a membrane having a Bubble Point pore size of no more than 1.0 μm while still providing a relatively high water volume flux.

Optionally, the method can further provide that a relatively high percentage of the biological organisms of the sample are retained on the surface of the membrane rather than being imbedded in pores of the membrane. Thus, in some embodiments, the method further provides that a relatively high percentage of the biological organisms retained on the surface of the membrane may be easily recovered from the membrane surface. In other cases, the method can further provide that the volume of the liquid sample is significantly reduced.

The following terms shall have the indicated meanings.

"Active" refers to filtration methods in which a mechanized force (e.g., a vacuum) drives the movement of liquid sample through a filter membrane.

"Biological analyte" refers to a molecule, or a derivative thereof, that occurs in or is formed by an organism. For example, a biological analyte can include, but is not limited to, at least one of an amino acid, a nucleic acid, a polypeptide, a protein, a polynucleotide, a lipid, a phospholipid, a saccharide, a polysaccharide, or any combination of two or more thereof. Exemplary biological analytes can include, but are not limited to, a metabolite (e.g., staphylococcal enterotoxin), an allergen (e.g., a peanut allergen), a hormone, a toxin (e.g., *Bacillus* diarrheal toxin, aflatoxin, etc.), RNA (e.g., mRNA, total RNA, tRNA, etc.), DNA (e.g., plasmid DNA, plant DNA, etc.), a tagged protein, an antibody, an antigen, or any combination of two or more thereof.

"Bubble Point pore size" refers to a computed average pore size of a membrane. Bubble Point pore size is based on the fact that liquid is held in the pores of a filter by surface tension and capillary forces. The minimum pressure required to overcome surface tension and force liquid out of the pores is a measure of the pore diameter. The formula for computing Bubble Point pore size is:

$$D = \frac{4\sigma \cos\theta}{P}$$

where:
P=bubble-point pressure;
σ=surface tension of the liquid (72 dynes/cm for water);
θ=liquid-solid contact angle (which for water is generally assumed to be zero); and
D=diameter of the pore.

"Elute" and variations thereof refer to removing biological organisms from a filter membrane using low stringency physical methods such as, for example, gravity, manual shaking, or vortexing.

"Entrapped" refers to biological organisms captured by a filter membrane that are not easily eluted from the filter membrane because, for example, the biological organisms are captured in spaces within the membrane.

"Passive" refers to filtration in which no mechanized force (e.g., a vacuum) drives the movement of liquid sample through a filter membrane. Passive filtration methods include filtration using, for example, gravity and/or absorption of fluid by an absorbent to drive the movement of fluid through a filter membrane.

"Recovered" refers to biological organisms that are eluted from a filter membrane in condition for detection and/or further analysis.

"Retained" and variations thereof refer to biological organisms that are disposed on the filter membrane surface after filtration and are easily eluted from the filter membrane.

"Water volume flux" refers to a volume of fluid passing through a unit area of membrane per unit time per unit of pressure. Unless otherwise indicated, water volume flux is expressed herein as liters of liquid sample passing through one square meter of membrane per hour per pound per square inch of pressure ($L/m^2 \cdot h \cdot psi$).

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Many commercially available membranes are used for filtering and removing biological organisms from liquid samples. The art of membrane filtration is well known. Existing commercially available membranes, however, typically have a torturous path and possess significant amount of large pores at the surface. This feature makes it difficult to recover filtered biological organisms because the captured biological organisms may become lodged in the pores of the filter membrane and are, therefore, difficult to remove from the filter intact so that the captured biological organisms may be analyzed.

Here, we describe methods in which liquid samples may be filtered using a filter membrane so that each of two competing parameters are satisfied. First, the methods involved retaining biological organisms on the surface of the filter membrane so that the retained biological organisms may be easily eluted from the membrane for further analysis. However, existing methods designed to capture high percentages of biological organisms do so by using membranes having very small average pore size. This necessarily limits the water flux volume and, consequently, the rate at which a given volume of liquid sample may be processed. Thus, the methods described herein further provide a greater water flux volume than presently observed in filtration methods.

In some cases, the method can involve filtering large volumes (e.g., multiple liters) of liquid sample such as may be desired for, for example, environmental testing, water quality testing, water treatment testing, and/or testing of repaired and/or restored water utility pipes. For example, using present methods for testing the water quality in repaired and/or restored water pipes, it can take two to three days to confirm that the water quality is sufficient to restore water service. Using the methods described herein, however, it may be possible to confirm water quality rapidly enough that water service can be restored within 24 hours.

In other cases, the method can involve filtering enriched food samples, food processing water samples, and/or potable water samples.

The methods described herein can decrease the time required for such testing in at least two ways. First, the methods permit large volumes of liquid sample to be filtered and analyzed. Second, the methods result in a significant percentage of the captured biological organisms being retained on the surface of the filter membrane so that they are more readily recovered by elution.

In other applications, the methods can involve relatively rapid filtration of smaller volumes of liquid samples (e.g., less than one liter). In these applications, too, the combination of relatively high water flux volume and retaining biological organisms on the filter membrane for easy recovery promotes more rapid and/or simpler filtration of liquid samples. In some of these applications, biological organisms may be recovered using simple gravity to dislodge retained biological organisms from the filter membrane. In other applications, a liquid sample may be significantly concentrated—i.e., some quantity less than the entire liquid volume may be passed through the filter membrane. Because a significant percentage of the biological organisms are retained on the filter membrane rather than being entrapped within the filter membrane, a greater percentage of the biological organisms in the original sample may be recovered in the remaining liquid volume, thereby concentrating the biological organisms for further identification and/or other analyses.

Generally, the methods include passing a sample comprising at least one biological organism through a filter membrane having a Bubble Point pore size of no more than 1.0 µm, thereby retaining at least one biological organism on the surface of the membrane. The methods include passing the sample through the filter membrane at a water volume flux of at least 10 L/m²·h·psi for passive filtration, or a water volume flux of at least 100 L/m²·h·psi for active filtration. The method further includes detecting the at least one biological organism retained on the surface of the filter membrane.

The liquid sample may be obtained from any suitable source, and may include a water sample. Exemplary water samples include environmental samples (e.g., lakes, rivers, streams, oceans, ponds, etc.), water utility/water treatment samples (e.g., water supply pipes, water treatment facilities, water treatment discharge, sewage, etc.), potable water samples (e.g., bottled water, well water) or food samples (e.g., liquid foods, food samples processed by, for example, homogenizing, etc.). Samples may be filtered as collected or may be processed to some degree prior to filtration and further analysis.

The biological organism may be any prokaryotic or eukaryotic organism for which detection and/or quantitation in a liquid sample may be desired. Accordingly, the biological organism may include, for example, a parasite, or a microbe such as, for example, a unicellular eukaryotic organism (e.g., a yeast), an algae, or a bacterium. Exemplary microbes include, for example, coliform bacteria. Exemplary bacterial species include, for example, *Escherichia* spp. (e.g., *E. coli*), *Enterobacter* spp. (e.g., *E. aerogenes*) *Enterococcus* spp., (e.g., *E. faecalis*), *Citrobacter* spp., (e.g., *C. freundii*), *Klebsiella* spp., *Shigella* spp., *Salmonella* spp. (e.g., *S. enterica*), *Listeria* spp, *Pseudomonas* spp., etc.

The filter membrane may possess a Bubble Point pore size of no more than 1.0 µm, although the methods may be performed using a filter membrane having a Bubble Point pore size of greater than 1.0 µm. Exemplary filter membranes can have a Bubble Point pore size of, for example, no more than 0.95 µm, no more than 0.9 µm, no more than 0.85 µm, no more than 0.8 µm, no more than 0.75 µm, no more than 0.7 µm, no more than 0.6 µm, or no more than 0.5 µm. Suitable Bubble Point pore sizes may be determined, at least in part, by, for example, the size of biological organism that is desired to be detected, the volume of sample to be filtered, and the depth of the filter membrane's pores. In the context of multi-zone membranes, The Bubble Point pore size is measured for the zone positioned to retain biological organisms.

Exemplary filter membranes can be made by, for example, TIPS (thermally induced phase separation) process, SIPS (solvent induced phase separation) process, VIPS (vapor induced phase separation) process, stretching process, track-etching, or electrospinning (e.g., PAN fiber membranes). Suitable membrane materials include, for example, polyolefins (e.g., polyethylene and/or polypropylene), ethylene-chlorotrifluoroethylene copolymer, polyacrylonitrile, polycarbonate, polyester, polyamide, polysulfone, polyethersulfone, polyvinylidene fluoride (PVDF), cellulose ester, and/or combinations thereof.

Suitable membranes may be characterized as porous membranes or as nanofiber membranes. Nanofiber filter membranes can have the fiber diameter less than 5 µm such as, for example, less than 1 µm. Nanofiber membranes may be prepared from, for example, polyacrylonitrile, polyvinylidene fluoride, a cellulose ester, polyvinyl acetate, polyvinyl alcohol, polyvinyl butyral, and/or combinations thereof.

Certain TIPS polyolefin membranes can be prepared so that they possess a single, homogeneous zone of membrane structure, each zone having a different pore microstructure. In other cases, a TIPS membrane may be prepared as a multi-zone membrane that includes two or more zones, each zone having a different pore microstructure. A multi-zone TIPS membrane may contain distinct zones or, alternatively, may possess a transition zone between two otherwise distinct zones.

Exemplary filter membranes include membranes and methods for making exemplary filter membranes are described in, for example, in U.S. Pat. No. 4,539,256, U.S. Pat. No. 4,726,989, U.S. Pat. No. 4,867,881, U.S. Pat. No. 5,120,594, U.S. Pat. No. 5,260,360, International Patent Publication No. WO2010/078234, International Patent Publication No. WO2010/071764, U.S. Provisional Patent Application Ser. No. 61/351,441, entitled, "Coated Porous Materials," filed Jun. 4, 2010, and U.S. Provisional Patent Application Ser. No. 61/351,447, entitled, "Process for Making Coated Porous Materials," filed Jun. 4, 2010.

In some cases, active filtration can provide a water flux volume of at least 100 L/m²·h·psi, although the methods may be performed at a water flux volume less than 100 L/m²·h·psi. Exemplary water flux volume values using active filtration include, for example, at least 250 L/m²·h·psi, at least 500 L/m²·h·psi, at least 750 L/m²·h·psi, at least 1000 L/m²·h·psi, at least 1250 L/m²·h·psi, at least 1500 L/m²·h·psi, at least 1750 L/m²·h·psi, at least 2000 L/m²·h·psi, at least 2500 L/m²·h·psi, or at least 3000 L/m²·h·psi. The maximum water flux rate may be determined, at least in part, by the maximum capacity of the mechanized force used to drive movement of the liquid sample through the filter membrane, the strength and/or durability of the filter membrane, and the Bubble Point pore size of the filter membrane.

In some cases, passive filtration can provide a water flux volume of at least 10 L/m²·h·psi, although the methods may be performed at a water flux volume less than 10 L/m²·h·psi. Exemplary water flux volume values using active filtration include, for example, at least 10 L/m²·h·psi, at least 20 L/m²·h·psi, at least 25 L/m²·h·psi, at least 32 L/m²·h·psi, at least 50 L/m²·h·psi, at least 60 L/m²·h·psi, at least 75 L/m²·h·psi, at least 88 L/m²·h·psi, at least 95 L/m²·h·psi, or at least 100 L/m²·h·psi. The maximum passive water flux rate may be determined, at least in part, by the Bubble Point pore size of the filter membrane and/or the flux gradient generated by, for example, an absorbent material positioned in fluid communication with the filter membrane so that it is capable of drawing at least a portion of the fluid sample through the filter membrane.

In some embodiments, the method results in at least 30% of the biological organisms in the sample are retained by the filter membrane, although the methods may be practiced so that fewer than 30% of the biological organisms in the sample being retained by the filter membrane. In exemplary methods, at least 40%, at least 45%, at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 97.5%, at least 98.5%, at least 99%, at least 99.1%, at least 99.2%, at least 99.3%, at least 99.4%, at least 99.5%, at least 99.6%, at least 99.7%, at least 99.8%, or at least 99.9% of the biological organisms in the sample are retained by the filter membrane.

Figure 7:
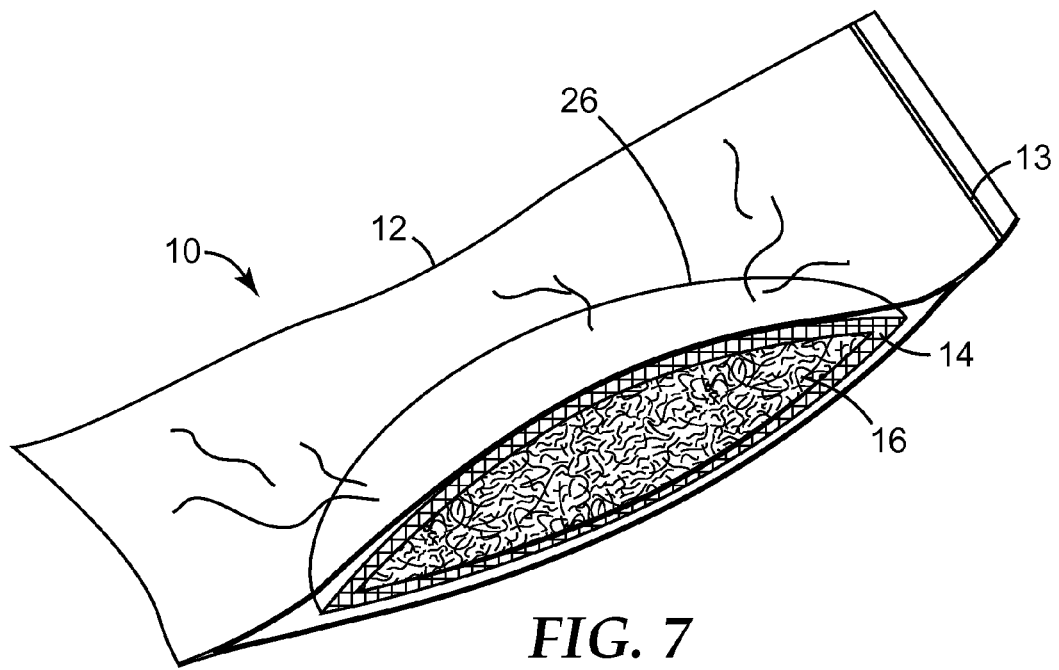
FIG. 7. A perspective schematic view of one embodiment of a filtration device.

As noted above, some embodiments can include, for example, a filter membrane in functional communication with an absorbent member within a larger device. Embodiments of such devices 10 are shown in FIGS. 7-13. In such embodiments, an absorbent member 16 can generate a water flux gradient sufficient to draw liquid across the filter membrane and into the absorbent member 16. In some embodiments (e.g., as shown in FIG. 7), the filter membrane can cover at least a portion of the absorbent member 16 so that flow of liquid into the absorbent member 16 requires that the liquid flow through the filter membrane. In this manner, biological organisms in the liquid sample may be retained by the filter membrane. The device 10 further comprises a container 12 with an optional closure 13. The container 12 may comprise a flexible, deformable container 12 such as a ZIPLOK brand storage bag, for example, having a sealable closure 13 comprised of interlocking components (13a and 13b).

Figure 8:
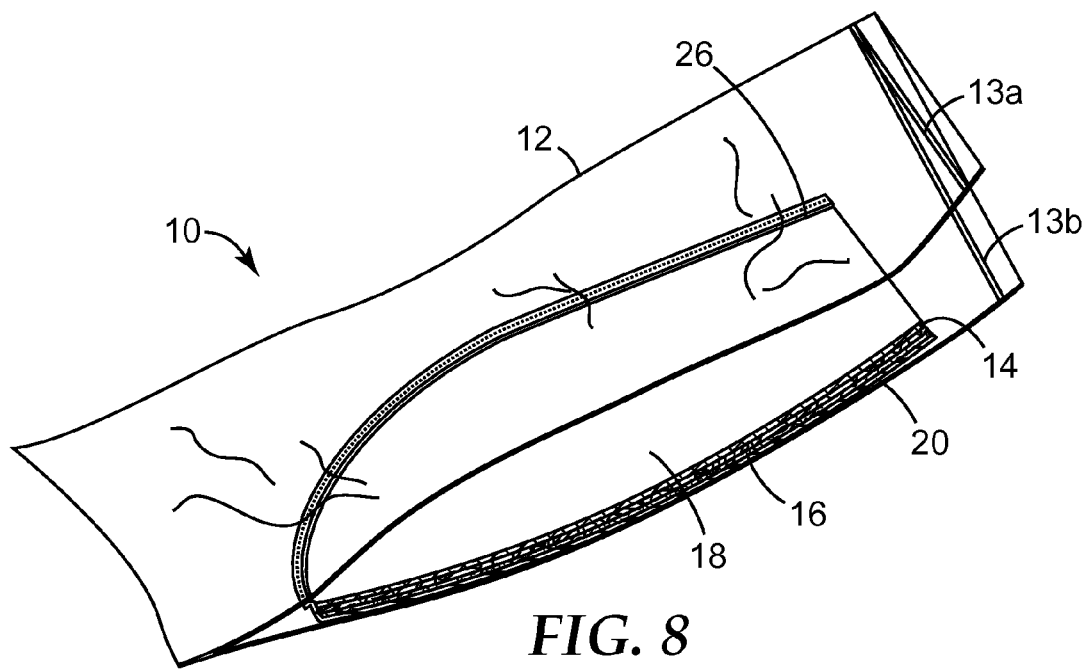
FIG. 8. A schematic side view of one embodiment of a filtration device.
Figure 9:
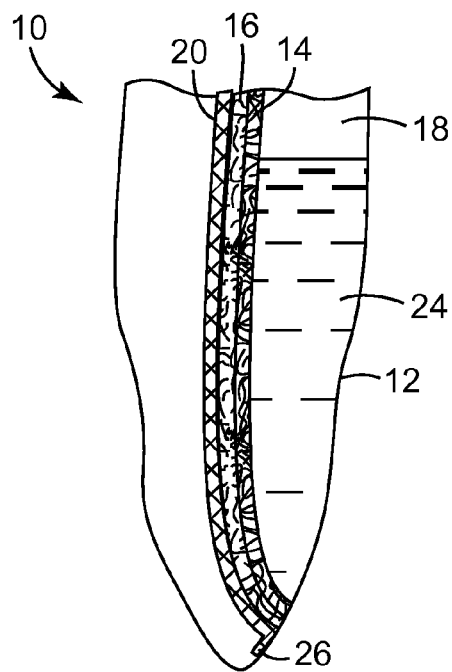
FIG. 9. A schematic side view of one embodiment of a filtration device.
Figure 10A:
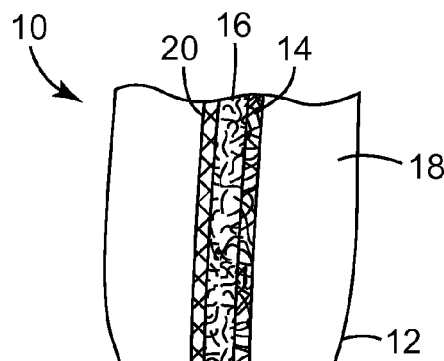
FIG. 10A. A schematic side view of one embodiment of a filtration device.
Figure 10B:
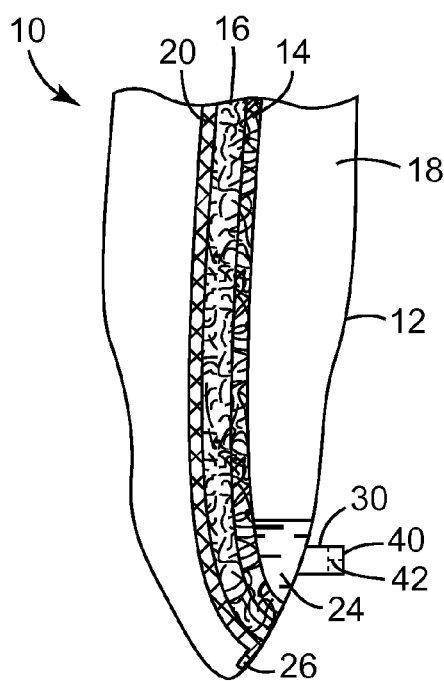
FIG. 10B. A schematic side view of one embodiment of a filtration device with a sample-retrieval port.

In one particular embodiment, shown in FIG. 8, the absorbent member 16 may be disposed on a surface of a pocket 18 formed in a device 10. The pocket 18 may, therefore, function as a receptacle for the liquid sample 24. The absorbent member 16 can optionally include a nonwoven backing 20 to assist in forming a seal 26, thereby fastening the absorbent member 16 to a portion of the container 12. The seal 26 may be formed via an adhesive or by heat-bonding, for example. The filter membrane 14 may be disposed on the open-pocket surface (i.e., facing the interior volume of the pocket 18) of the absorbent member 16. In use, illustrated in FIGS. 9 and 10A-B, the device 10 may be oriented so that the filter membrane 14 is in a generally vertical orientation. In some cases, therefore, biological organisms retained by the filter membrane 14 may elute from the filter membrane 14 due to gravity. Thus, as liquid is absorbed by the absorbent member 16, biological organisms in the liquid sample 24 are concentrated. When the liquid sample 24 reaches a volume corresponding to a desired level of concentration of the biological organisms, a portion of the concentrated liquid sample 24 (FIG. 10A) may be removed from the device 10 by using, for example, a syringe 22. The removed portion of the concentrated liquid sample may then be subjected to further analysis.

In some embodiments, a portion of the concentrated liquid sample 24 (FIG. 10B) may be removed from the device 10 by using, for example, a sample port 30 to obtain the concentrated liquid sample 24. The sample port 30 may include an elastically-deformable split septum 40 (e.g., a split-cap TPE plug style cap available from Micronic North America, LLC; McMurray, Pa.), comprising a slit 42 through which a pipette tip (not shown) can be inserted to recover all or a portion of the concentrated liquid sample 24. In some embodiments (not shown), the sample port may comprise a valve that can be opened to release a portion (or all) of the concentrated liquid sample by gravity flow, for example.

Figure 13:
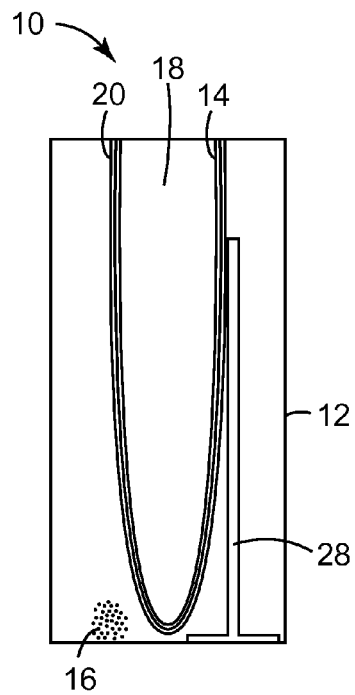
FIG. 13. A cross-sectional schematic side view of an embodiment of a filtration device with a support member, according to the present disclosure.

FIG. 13 shows another embodiment of a device 10 according to the present disclosure. In this embodiment, material used for the filter membrane 14 is configured to form a pocket 18 (e.g., by sealing together all but a portion of the edges of two sheets of filter membrane material) disposed inside a container 12 (e.g., a ZIPLOK bag). The pocket 18 has in interior volume defined by the filter membrane 14. Optionally, the pocket 18 may further comprise an exterior nonwoven backing 20 to provide structural support for the filter membrane 14. An absorbent member 16 is placed in a portion of container 12 outside of the pocket 18 formed by the filter membrane 14. Preferably, the absorbent member 16 is proximate the pocket 18. More preferably, the absorbent member 16 contacts at least a portion of the filter membrane 14 external to the pocket 18. Even more preferably, the absorbent member 16 is disposed on at least a portion of the filter membrane 14 external to the pocket 18. In some embodiments, the absorbent member 16 is disposed between the filter membrane and the nonwoven backing 20. Optionally, the device 10 further can comprise a support member 28 (e.g., a molded plastic rod with a base) that can be used to provide structural support for a relatively flexible container 12 before, during, and after the addition of a liquid sample. In use, the device 10 can be held (e.g., either manually or via a support member) while a liquid sample (not shown) is placed into the pocket 18. After a portion of the liquid sample passes through the filter membrane 14, the concentrated liquid sample (not shown) can be removed from the pocket 18 using a pipette, for example.

An alternative embodiment (not shown) of the device illustrated in FIG. 13 comprises a device in which the absorbent member is disposed in the interior volume of the pocket and the sample is deposited into the container external to the pocket. In use, the sample is deposited into the container rather than into the pocket. After at least a portion of the liquid sample has passed through the filter membrane, all or a portion of the remainder of the liquid sample in the container can be withdrawn from the container for detection of a biological organism using any of the detection methods disclosed herein.

The absorbent member 16 may be constructed of any suitable fluid-absorbing material. In some cases, the absorbent member 24 can include a hydrogel. As used herein, the term "hydrogel" refers to a polymeric material that is hydrophilic and that is either swollen or capable of being swollen with a polar solvent. Suitable hydrogels include crosslinked hydrogels, swollen hydrogels, and dried or partially-dried hydrogels.

Suitable hydrogels include polymers comprising ethylenically unsaturated carboxyl-containing monomers and co-monomers selected from carboxylic acids, vinyl sulfonic acid, cellulosic monomer, polyvinyl alcohol, as described in U.S. Patent Application Publication No. US2004/0157971; polymers comprising starch, cellulose, polyvinyl alcohol, polyethylene oxide, polypropylene glycol, and copolymers thereof, as described in U.S. Patent Application Publication No. US 2006/0062854; the hydrogels, and polymeric beads made therefrom, described in International Patent Publication No. WO 2007/146722; polymers comprising polyurethane prepolymer with at least one alcohol selected from polyethylene glycol, polypropylene glycol, and propylene glycol, as described in U.S. Pat. No. 6,861,067; and polymers comprising a hydrophilic polymer selected from polysaccharide, polyvinylpyrolidone, polyvinyl alcohol, polyvinyl ether, polyurethane, polyacrylate, polyacrylamide, collagen and gelatin, as described in U.S. Pat. No. 6,669,981, the disclosures of which are all herein incorporated by reference in their entirety. Other suitable hydrogels include agar, agarose, and polyacrylamide hydrogels. In certain embodiments, the hydrogel can include crosslinked polyacrylic acid sodium salt/copolymer, polyacrylamide copolymer, ethylene maleic anhydride copolymer, cross-linked carboxy-methyl-cellulose, polyvinyl alcohol copolymers, cross-linked polyethylene oxide, starch grafted copolymer of polyacrylonitrile, or any combination thereof.

The hydrogels can include a shaped hydrogel. Shaped hydrogels include hydrogels shaped into, for example, beads, sheets, ribbons, and fibers.

The hydrogels can further include supported hydrogels. Supported hydrogels include hydrogels disposed on and/or in beads, nonwoven sheets, fibers (e.g., blown microfibers), and the like.

In some embodiments, the volume of the concentrated sample may be less than 50% of the volume of the sample added to the device, although the method may be practiced while reducing the volume of the sample to a lesser extent. Exemplary degrees of volume reduction can include, for example, the concentrated sample having a volume that is less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, or less than 0.01% of the volume of the sample added to the device. In one exemplary embodiment, an initial sample of 225 ml may be reduced to a volume of approximately 2 ml, so that the concentrated sample possesses a volume of approximately 0.09% of the volume of the liquid sample added to the device.

The methods further include detecting at least one biological organism retained by the filter membrane. In this context, a biological organism retained by the filter membrane includes biological organisms that are in contact with the filter membrane as well as biological organisms subsequently recovered from the filter membrane. Biological organisms may be recovered from the filter membrane by any suitable method. One feature of biological organisms retained on the filter membrane by practicing the methods described herein is that the retained biological organisms may be removed from the filter membrane using relatively low stringency physical methods such as, for example, gravity, manual shaking, and/or vortexing. So, for example, in embodiments just described in which the volume of liquid sample is reduced, biological organisms concentrated in the reduced volume of the liquid sample may be considered recovered from the filter membrane, even if the biological organisms did not reside in or on the filter membrane for any discernable length of time.

Thus, in some embodiments, retained biological organisms may be detected in situ while still in contact with the filter membrane. In other embodiments, however, the retained biological organisms may be removed from the filter membrane and the biological organisms so recovered may be detected. Whether detected in situ or following recovery from the filter membrane, the biological organisms may be detected using any suitable method including those routine to those of ordinary skill in the art of microbial detection. Suitable in situ detection methods include, for example, detecting biological organism-specific binding of an antibody composition (e.g., monoclonal or polyclonal antibodies). Other detection methods can include, for example, detecting the presence of a biological analyte produced by the biological organism. Exemplary detection methods include, but are not limited to, detecting amplified (by, for example, PCR) biological organism-specific nucleotides sequences, nucleotide sequencing, enzyme assays (e.g., detection of dehydrogenases, glucoronidases, β-galactosidases, proteases, etc.), bioluminescence assays (e.g., detection of ATP/ADP/AMP), detection of proteins/peptides, spectrometry, and/or fluorescence (e.g., detection of NAD/NADH, FAD/FADH, autofluorescence), and the like. Suitable detection methods for biological organisms recovered from the filter membrane include methods applicable for in situ detection of biological organisms, and further includes detecting growth in culture.

In some cases, the method can further include quantifying biological organisms retained by the filter membrane. In this context, too, a biological organism retained by the filter membrane includes biological organisms that are in contact with the filter membrane as well as biological organisms subsequently recovered from the filter membrane.

Thus, in some embodiments, retained biological organisms may be quantified in situ while still in contact with the filter membrane. In other embodiments, however, the retained biological organisms may be removed from the filter membrane and the biological organisms so recovered may be quantified. Whether quantified in situ or following recovery from the filter membrane, the biological organisms may be quantified using any suitable method including those routine to those of ordinary skill in the art of microbial detection such as, for example, colony forming unit (cfu) detection, most probable number (MPN) analysis, ATP bioluminescence, enzyme assays, PCR, reverse transcriptase PCR (RT-PCR), quantitative PCR, and the like.

In embodiments in which the biological organisms are detected and/or quantified following recovery from the filter membrane, the method includes eluting at least 50% of the retained biological organisms from the filter membrane, although the method may be performed after eluting less than 50% of the retained biological organisms from the filter membrane. In exemplary methods, at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 97.5%, at least 98.5%, at least 99%, at least 99.1%, at least 99.2%, at least 99.3%, at least 99.4%, at least 99.5%, at least 99.6%, at least 99.7%, at least 99.8%, or at least 99.9% of the retained biological organisms are eluted from the filter membrane.

In some cases, the retained biological organisms are eluted by repositioning the filter membrane so that the force of gravity causes the retained biological organisms to dislodge and thereby elute from the filter membrane. In other cases, retained biological organisms may be eluted from the filter membrane by manually shaking the filter membrane to dislodge the retained biological organisms from the filter membrane. In other cases, retained biological organisms may be eluted by vortexing the filter membrane to dislodge the retained biological organisms from the filter membrane. In other cases, biological organisms may be eluted from the filter membrane by foam elution as described in Example 12, below.

Certain existing methods provide recovery of up to about 30% of biological organisms (e.g., bacteria) and, therefore, fail to provide the same degree of recovery as observed using the methods described herein.

Without wishing to be bound by any particular theory, certain existing methods may fail to provide satisfactory recovery of biological organisms because the microporous filter membranes possess a significant amount of large pores at the surface of the membrane even when the filter membranes have a pore rating smaller than the size of bacteria. The large pores are believed to entrap the biological organisms rather than retain the biological organisms while the sample volume is being reduced.

In addition, nonspecific binding of, for example, bacteria to the surface of the filter membrane creates a challenge. This is due, at least in part, because one way to reduce the volume of a liquid sample more quickly is to provide a greater surface area of filter membrane through which liquid may be absorbed. Increasing the surface are, however, also increases the surface area to which biological organisms may bind nonspecifically. Many alternatives were investigated. However, none of the membranes was able to provide both a high retention rate of biological organisms (and, therefore, high recovery rate) and a good water flux volume (e.g., sufficient to concentrate from 225 ml to 2-3 ml in, for example, less than one hour.

In certain embodiments, the method can provide a reduction in sample volume of about 98.6% to about 99.2% while permitting recovery of at least 70% of biological organisms in the original sample.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Preparation of TIPS Membranes

R1901-11 Membrane

A multi-zone microporous polypropylene membrane (designated herein as R1901-11) was prepared as described in International Patent Publication No. WO2010/078234 using both a 40 mm twin screw extruder and a 25 mm twin screw extruder. Melt streams from the two extruders were cast into a single sheet through a multi-manifold die.

Melt stream 1. Polypropylene (PP) resin pellets (F008F from Sunoco Chemicals, Philadelphia, Pa.) and a nucleating agent (MILLAD 3988, Milliken Chemical, Spartanburg, S.C.) were introduced into a 40 mm twin screw extruder which was maintained at a screw speed of 250 rpm. The mineral oil diluent (Mineral Oil SUPERLA White 31, Chevron Corp., San Ramon, Calif.) was fed separately from the reservoir into the extruder. The weight ratio of PP/diluent/nucleating agent was 29.25%/70.7%/0.05%. The total extrusion rate was about 30 lb/hr (13.6 kg/hr) and the extruder's eight zones were set to provide a decreasing temperature profile from 271° C. to 177° C.

Melt stream 2. PP resin pellets and MILLAD 3988 were introduced into a 25 mm twin screw extruder which was maintained at a screw speed of 125 rpm. The mineral oil diluent was fed separately from the reservoir into the extruder. The weight ratio of PP/diluent/nucleating agent was 29.14%/70.7%/0.16%. The total extrusion rate was about 6 lb/hr (2.72 kg/hr) and the extruder's eight zones were set to provide a decreasing temperature profile from 271° C. to 177° C.

The multi-zone film was cast from the multi-manifold die maintained at 177° C. onto a patterned casting wheel. The temperature of casting wheel was maintained at 60° C. and the casting speed was 3.35 m/min (11 ft/min). The resulting film was washed in-line in a solvent to remove mineral oil in the film and then air dried. The washed film was sequentially oriented in the length and cross direction 1.8×2.80 at 99° C. and 154° C., respectively.

R1901-8B Membrane

A multi-zone microporous polypropylene membrane (designated herein as R1901-8B) was prepared as described in International Patent Publication No. WO2010/078234 using both a 40 mm twin screw extruder and a 25 mm twin screw extruder. Melt streams from the two extruders were cast into a single sheet through a multi-manifold die.

Melt stream 1. Polypropylene (PP) resin pellets (F008F from Sunoco Chemicals, Philadelphia, Pa.) and a nucleating agent (MILLAD 3988, Milliken Chemical, Spartanburg, S.C.) were introduced into a 40 mm twin screw extruder which was maintained at a screw speed of 250 rpm. The mineral oil diluent (Mineral Oil SUPERLA White 31, Chevron Corp., San Ramon, Calif.) was fed separately from the reservoir into the extruder. The weight ratio of PP/diluent/nucleating agent was 29.254%/70.7%/0.045%. The total extrusion rate was about 27 lb/hr (12.2 kg/hr) and the extruder's eight zones were set to provide a decreasing temperature profile from 271° C. to 177° C.

Melt stream 2. PP resin pellets and MILLAD 3988 were introduced into a 25 mm twin screw extruder which was maintained at a screw speed of 125 rpm. The mineral oil diluent was fed separately from the reservoir into the extruder. The weight ratio of PP/diluent/nucleating agent was 28.146%/70.7%/0.154%. The total extrusion rate was about 9 lb/hr (4.08 kg/hr) and the extruder's eight zones were set to provide a decreasing temperature profile from 271° C. to 177° C.

The multi-zone film was cast from the multi-manifold die maintained at 177° C. onto a patterned casting wheel. The temperature of casting wheel was maintained at 60° C. and the casting speed was 3.52 m/min (11.54 ft/min). The resulting film was washed in-line in a solvent to remove the mineral oil diluent and then air dried. The washed film was sequentially oriented in the length and cross direction 1.6×2.85 at 99° C. and 154° C., respectively.

R1933-7 Membrane

A multi-zone microporous polypropylene membrane (designated herein as R1933-7) was prepared as described in International Patent Publication No. WO2010/078234 using both a 40 mm twin screw extruder and a 25 mm twin screw extruder. Two melt streams from extruders were cast into a single sheet through a multi-manifold die.

Melt stream 1. Polypropylene (PP) resin pellets (F008F from Sunoco Chemicals, Philadelphia, Pa.) and a nucleating agent (MILLAD 3988, Milliken Chemical, Spartanburg, S.C.) were introduced into a 40 mm twin screw extruder which was maintained at a screw speed of 175 rpm. The mineral oil diluent (Kaydol 350 Mineral Oil, Brenntag Great Lakes LCC, St. Paul, Minn.) was fed separately from a reservoir into the extruder. The weight ratio of PP/diluent/nucleating agent was 34.247%/65.7%/0.053%. The total extrusion rate was about 32 lb/hr (14.5 kg/hr) and the extruder's eight zones were set to provide a decreasing temperature profile from 271° C. to 177° C.

Melt stream 2. PP resin pellets and MILLAD 3988 were introduced into a 25 mm twin screw extruder which was maintained at a screw speed of 150 rpm. The mineral oil diluent was fed separately from the reservoir into the extruder. The weight ratio of PP/diluent/nucleating agent was 29.14%/70.7%/0.16%. The total extrusion rate was about 6 lb/hr (2.72 kg/hr) and the extruder's eight zones were set to provide a decreasing temperature profile from 254° C. to 177° C.

The multi-zone film was cast from the multi-manifold die maintained at 177° C. onto a patterned casting wheel. The temperature of casting wheel was maintained at 71° C. and the casting speed was 5.79 m/min (19.00 ft/min). The resulting film was washed in-line in a solvent to remove mineral oil diluent and then air dried. The washed film was sequentially oriented in the length and cross direction 1.5×2.70 at 99° C. and 160° C., respectively.

R1933-18 Membrane

A multi-zone microporous polypropylene membrane (designated herein as R1933-18) was prepared as described in International Patent Publication No. WO2010/078234 using both a 40 mm twin screw extruder and a 25 mm twin screw extruder. Two melt streams from extruders were cast into a single sheet through a multi-manifold die.

Melt stream 1. Polypropylene (PP) resin pellets (F008F from Sunoco Chemicals, Philadelphia, Pa.) and a nucleating agent (MILLAD 3988, Milliken Chemical, Spartanburg, S.C.) were introduced into the hopper using a solids feeder and the materials were fed into of a 40 mm twin screw extruder which was maintained at a screw speed of 175 rpm. The mineral oil diluent (Kaydol 350 Mineral Oil, Brenntag Great Lakes LCC, St. Paul, Minn.) was fed separately from a reservoir into the extruder. The weight ratio of PP/diluent/nucleating agent was 34.247%/65.7%/0.053%. The total extrusion rate was about 32 lb/hr (14.5 kg/hr) and the extruder's eight zones were set to provide a decreasing temperature profile from 271° C. to 177° C.

Melt stream 2. PP resin pellets and MILLAD 3988 were introduced into a 25 mm twin screw extruder which was maintained at a screw speed of 150 rpm. The mineral oil diluent was fed separately from the reservoir into the extruder. The weight ratio of PP/diluent/nucleating agent was 28.98%/70.7%/0.32%. The total extrusion rate was about 6 lb/hr (2.72 kg/hr) and the extruder's eight zones were set to provide a decreasing temperature profile from 260° C. to 194° C.

The multi-zone film was cast from the multi-manifold die maintained at 177° C. onto a patterned casting wheel. The temperature of casting wheel was maintained at 52° C. and the casting speed was 5.84 m/min (19.15 ft/min). The resulting film was washed in-line in a solvent to remove the mineral oil diluent and then air dried. The washed film was sequentially oriented in the length and cross direction 1.7×2.75 at 99° C. and 160° C., respectively.

Example 2

Surface Coating of TIPS Membranes

A 4-wt % SPAN20 (Uniqema, New Castle, Del.) solution was prepared by dissolving the surfactant in 2-propanol (Alfa Aesar, Ward Hill, Mass.).

A TIPS microporous membrane was saturated with the above surfactant solution in a polyethylene (PE) bag. The membrane saturated instantly and excessive surface solution was removed by rubbing the PE bag. The membrane was removed from the bag and exposed to air to completely dry the membrane. The dried membranes were stored in a PE bag at room temperature.

Example 3

Surface Modification of TIPS Membranes

The TIPS membranes were coated with polyethylene glycol (PEG) as described in U.S. Provisional Patent Application Ser. No. 61/351,447, entitled, "Process for Making Coated Porous Materials," filed Jun. 4, 2010.

A 5-wt % EVAL stock solution was made by dissolving an ethylene-vinyl alcohol copolymer (EVAL) with 44 mol % ethylene content (EVAL44, Sigma-Aldrich Co., St Louis, Mo., USA) in an ethanol (AAPER Alcohol and Chemical Co. Shelbyville, Ky.)/water solvent mixture (70 vol % ethanol) in a water bath at temperature 70-80° C.

From the above stock solution, a solution was made containing 1-wt % EVAL44, 2-wt % SR@610 (Sartomer, Warrington, Pa.), 1 wt % reactive photoinitiator VAZPIA (2-[4-(2-hydroxy-2-methylpropanoyl)phenoxy]ethyl-2-methyl-2-N-propenoylamino propanoate, as disclosed in U.S. Pat. No. 5,506,279) in ethanol/water mixture solvent (70 vol % ethanol)

A TIPS microporous membrane was saturated with the coating solution above in a heavy weight PE bag. Effort was made to remove the excessive surface solution by paper towel wiping after the saturated membrane was removed from the PE bag. The membrane was allowed to dry by solvent evaporation at room temperature for 10-12 hours. Then, the dry membrane was saturated with a 20-wt % NaCl aqueous solution. After that, the membrane went through a nitrogen inert Fusion UV system with H-bulb on a conveying belt. The speed of the belt was 20 feet per minute (fpm). The membrane was sent through the UV system again in the same speed with the opposite membrane side facing the light source. The cured membrane sample was washed in excessive deionized water and dried at 90° C. for 1 to 2 hours until completely dry. The dried membranes were stored in a PE bag at room temperature.

Example 4

Preparation of Polyacrylonitrile (PAN) Membranes

Various PAN membranes were made as disclosed in Korean Patent Application No. KR20040040692. A 10.5-wt % of polyacrylonitrile (Mw. 150,000) was prepared in N,N-dimethylacetamide (DMAC). Using a syringe pump, a constant flow of PAN polymer solution (50 µl/min/hole) was supplied into a syringe connected to a high voltage source. An electric force of 90-100 Kv was introduced to form an electrostatic force to cause the polymer solution ejection into air and formation of PAN nanofibers. After the electrospinning process, the collected PAN nanofibers had bulkiness similar to cotton and not like that of a film and/or a membrane. To reduce the bulkiness and to increase the structural integrity of the electrospun PAN nanofibers, a post-treatment (hot calendaring process) was carried out at 140° C. and 10-20 kgf/cm$^3$ pressure. The PAN nanofibers were stored as a roll in a PE bag at room temperature.

Example 5

Characterization of Membranes a) Water Flow Rate Measurement

A 47 mm disk of a membrane was cut using a die punch and the membrane disk was mounted in a Gelman magnetic holder (Gelman Sciences, Inc., Ann Arbor, Mich.). The active membrane diameter in the holder was 34 mm. One hundred ml of water was added to the holder and a vacuum pressure of about 23.5 inches of mercury was applied using a vacuum pump (GAST Manufacturing, Inc., Benton Harbor, Mich.) to draw water through the membrane. The time for the water to pass through the membrane was recorded with a stopwatch. The water flow rate (flux) was calculated using the time, vacuum pressure, and area of the membrane and expressed in $L/(m^2 \cdot h \cdot psi)$.

b) Bubble Point Pore Size Measurement

The Bubble Point pore size of a membrane was measured according to ASTM-F316-03. The membrane was pre-wetted with isopropanol or FC-43 (3M Co., St Paul, Minn.), or liquid GALWICK (PMI, Porous Materials, Inc., Ithaca, N.Y.) and mounted on a testing holder. Pressurized nitrogen gas was gradually applied to one side of the membrane until the gas flow detected at the other side reached 100%. The pressure at 100% gas flow through the membrane was recorded and used to calculated Bubble Point pore size.

TIPS membrane processing conditions are summarized in Table 1, below.

The water flux rate and Bubble Point pore size for various membranes are shown below in Table 2, below.

c) Scanning Electron Microscopy of Membranes

For PAN membranes, the filter from each of the samples was mounted on an aluminum stub. For TIPS membranes, two sections from each of the samples were removed and mounted on an aluminum stub to view both the "Tight" and "Open" surfaces. Cross sections of each of the TIPS membranes were also prepared by tearing under liquid nitrogen. These were mounted on an additional stub. All specimens were sputter coated with gold/palladium and were examined using a JEOL 7001F Field Emission Scanning Electron Microscope. Digital photomicrographs were the product of secondary electron imaging (SEI), a technique used to image surface morphology of a sample. All micrographs were taken at a viewing angle normal to the surface of the stub or sectioned face (nominally). Images were captured at various magnifications and the magnification is indicated on the images shown. The "Tight" and "Open" surfaces (also referred to as sides or zones) are indicated in the image for each cross section. A length marker is also shown in the lower portion of each micrograph of FIGS. 1-6.

TABLE 1

TIPS Membrane Processing Conditions

|  | R1930-10 | R1901-11 | R1901-8B | R1933-7 | R1933-18 |
|---|---|---|---|---|---|
| MS 1 Screw Speed | 150 rpm | 250 rpm | 250 rpm | 175 rpm | 175 rpm |
| MS 1 PP/DIL/NA ratio (weight %) | 29.23/70.70/0.072 | 29.25/70.7/0.05 | 29.25/70.7/0.045 | 34.25/65.7/0.053 | 34.25/65.7/0.053 |
| MS 1 Extrusion Rate | 21 lbs/hr (9.53 kg/h) | 30 lb/hr (13.6 kg/hr) | 27 lb/hr (12.2 kg/hr) | 32 lb/hr (14.5 kg/hr) | 32 lb/hr (14.5 kg/hr) |
| MS 1 Temp Profile | 271° C. to 204° C. | 271° C. to 177° C. | 271° C. to 177° C. | 271° C. to 177° C. | 271° C. to 177° C. |
| MS 2 Screw Speed | 150 rpm | 125 rpm | 125 rpm | 150 rpm | 150 rpm |
| MS 2 PP/DIL/NA ratio (weight %) | 29.15/70.70/0.15 | 29.14/70.7/0.16 | 29.15/70.7/0.15 | 29.14/70.7/0.16 | 28.98/70.7/0.32 |
| MS 2 Extrusion Rate | 9 lbs/hr (4.08 kg/h) | 6 lb/hr (2.72 kg/hr) | 9 lb/hr (4.08 kg/hr) | 6 lb/hr (2.72 kg/hr) | 6 lb/hr (2.72 kg/hr) |
| MS 2 Temp Profile | 271° C. to 204° C. | 271° C. to 177° C. | 271° C. to 177° C. | 254° C. to 177° C. | 260° C. to 194° C. |
| Die Temperature | 199° C. (390° F.) | 177° C. (350° F.) | 177° C. (350° F.) | 177° C. (350° F.) | 177° C. (350° F.) |
| Wheel temperature | 60° C. | 60° C. | 60° C. | 71° C. | 52° C. |
| Casting wheel speed | 13.0 ft/min (4.0 m/min) | 3.35 m/min (11 ft/min) | 3.52 m/min (11.54 ft/min) | 5.79 m/min (19.00 ft/min) | 5.84 m/min (19.15 ft/min) |
| Orientation - L × W | 1.70 × 3.35 | 1.8 × 2.80 | 1.6 × 2.85 | 1.5 × 2.70 | 1.7 × 2.75 |
| Orientation Temp-L/W |  | 99° C./154° C. | 99° C./154° C. | 99° C./54° C. | 99° C./160° C. |

TABLE 2

Membrane Properties
TIPS Membrane

| Membrane - treatment | Water flux (L/m²·h·psi) | Bubble Point pore size (μm) | Porosity | Tight zone thickness (μm) | Total thickness (μm) |
|---|---|---|---|---|---|
| R1930-10 - untreated | 937 | 0.34 | 84% | 16.0 | 53.3 |
| R1930-10 - SPAN20 | 917 | — |  | 16.0 | 53.3 |
| R1901-11 - untreated | 2723 | 0.74 | 85% | 8 | 104 |
| R1901-11 - SPAN20 | 2,739 | 0.74 |  | 8 | 104 |
| R1901-11 - PEG | 2427 | 0.62 | — | 8 | 104 |
| R1902-8B - untreated | 1832 | 0.51 | 84% | 23 | 109 |
| R1902-8B - SPAN20 | 1,945 | 0.51 | 84% | 23 | 109 |
| R1902-8B - PEG | 2091 | 0.49 | — | 23 | 109 |
| R1933-7 - untreated | 1263 | 0.34 | 77% | 12 | 74 |
| R1933-7 - SPAN20 | 680 | 0.34 | — | 12 | 74 |
| R1933-7 - PEG | 1401 | 0.34 | — | 12 | 74 |
| R1933-18 - untreated | 577 | 0.23 | — | 6 | 56 |
| R1922-18 - SPAN20 | 357 | — | — | 6 | 56 |
| Nanofiber filters |  |  |  |  |  |
| PAN-1 | 3995 | 0.613 | 62% | — | 11.1 |
| PAN-2 | 2430 | 0.531 | 62% | — | 16.9 |
| PAN-3 | 3436 | 0.367 | 70% | — | 15.5 |

Example 6

Bacteria Used in Examples

The various bacteria used in the examples (Table 3) were obtained from ATCC (Manassas, Va.).

TABLE 3

Bacteria used in examples

| Bacteria | ATCC No. |
|---|---|
| Enterococcus faecalis | 700802 |
| Escherichia coli | 51813 |
| Salmonella enterica subsp. enterica | 51812 |
| Citrobacter braakii | 10625 |
| Citrobacter freundii | 14135 |
| Enterobacter aerogenes | 29007 |
| Enterobacter cloacae | 10699 |

Pure cultures of the bacterial strains were inoculated into Tryptic Soy Broth (TSB, BD, Franklin Lakes, N.J.) and were grown overnight at 37° C. The cultures were diluted serially in Butterfield phosphate buffer (Whatman, Piscataway, N.J.) to obtain desired amount of colony forming units (cfu) per ml for spiking into water samples. The bacteria were quantified by plating appropriate dilutions on 3M PETRIFILM *E. coli*/Coliform Count Plates (3M Co., St. Paul, Minn.) according to manufacturer's instruction and incubated overnight at 37° C. The plates were read using 3M PETRIFILM Plate Reader (3M Co.) and colony forming units (cfu) were determined.

Example 7

Recovery of *E. coli* from Spiked Water Samples by Filtration Followed by Direct Growth

*E. coli* was grown over night in Tryptic Soy Broth (TSB) at 37° C. The culture was diluted to obtain approximately 100 cfu/ml and 1 ml of the solution was added to 1000 ml of sterile water to obtain approximately 100 cfu. A 47 mm membrane was cut from sheets or discs and placed on sterile glass filter holder assembly with funnel, flitted base (Millipore, Billerica, Mass.). The filter holder was connected to a 4 L vacuum filtering flask. The solution was filtered through the various membranes at vacuum pressure of about 20 inches of mercury using an AIR CADET Vacuum/Pressure Station (model No. 420-3901, Barnant Company, Barrington, Ill.). The membranes were removed aseptically and placed on blood agar or tryptic soy agar plates (Hardy Diagnostics, Santa Maria, Calif.) and incubated overnight at 37° C. The colonies growing on membranes were counted to determine colony forming units (cfu). The results obtained are shown below in Table 4. All the membranes tested showed greater than 73% recovery with the smaller pore size membranes (<0.5 μm) showing greater than 90% recovery.

TABLE 4

Recovery of *E. coli* from spiked water sample by filtration and direct growth

|  | Total cfu recovered | % Recovery |
|---|---|---|
| Input | 105 cfu |  |
| R1933-18/SPAN (0.23 μm) | 98 | 93.33 |
| R1933-7/SPAN (0.34 μm) | 95 | 90.48 |
| R1901-8B/SPAN (0.49 μm) | 92 | 87.62 |
| R1901-11/SPAN (0.74 μm) | 77 | 73.33 |
| PAN-1 (0.613 μm) | 80 | 76.19 |
| PAN-2 (0.531 μm) | 88 | 83.81 |
| PAN-3 (0.367 μm) | 100 | 95.24 |
| Isopore polycarbonate filter (0.40 μm) | 97 | 92.38 |
| MF-Millipore Type HAWP (0.45 μm) | 98 | 93.33 |

Example 8

Recovery of *E. coli* from Spiked Water Samples by Filtration Followed by Elution

*E. coli* was grown over night in TSB at 37° C. The culture was diluted to obtain approximately 100 cfu/ml and 1 ml of the solution was added to 1000 ml of sterile water to obtain approximately 100 cfu. A 47 mm membrane was cut from sheets or discs and placed on sterile vacuum filtration apparatus. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 5 ml of 0.2% Tween-20 (Sigma-Aldrich Co., St. Louis, Mo.) and vortexed (Fixed Speed Vortex Mixer, VWR, West Chester, Pa.) at room temperature for 1 to 2 minutes. The solution was plated on 3M PETRIFILM *E. coli*/Coliform Count Plates (3M Co., St. Paul, Minn.) according to manufacturer's instruction and incubated overnight at 37° C. The plates were read using 3M PETRIFILM Plate Reader (3M Co.) and colony forming units (cfu) were determined. The results obtained are shown below in Table 5. The results are representative of a typical experiment. From 1000 ml water samples spiked with about 100 cfu of *E. coli*, recoveries ranged from 28.6% to 72.9%. For the treated TIPS membranes and one PAN membrane (PAN-3) the recovery varied from 45% to 72.9%. The TIPS membrane R1933-18/SPAN (0.2 μm) had a low flux rate as it took 25 minutes to filter 1 liter of water. R1933-7/SPAN (0.34 μm) had a good flux rate. Both membranes showed good recovery of filtered bacteria. For the two commercial membranes the recovery ranged from 28.6 to 35.7%.

TABLE 5

Recovery of *E. coli* by filtration and elution from various membranes

|  | Total cfu recovered | % Recovery | Time to filter 1 liter 20 mm Hg vacuum (min:sec) |
|---|---|---|---|
| Input | 140 cfu |  |  |
| R1933-18/SPAN (0.2 μm) | 102 | 72.86 | 25:19 |
| R1933-7/Original (0.34 μm) | 54 | 38.57 | 5:28 |
| R1933-7/PEG (0.34 μm) | 87 | 61.90 | 6:01 |
| R1933-7/SPAN (0.34 μm) | 98 | 70.00 | 6:08 |
| R1901-8B/PEG (0.51 μm) | 68 | 48.81 | 2:50 |
| R1901-8B/SPAN (0.49 μm) | 78 | 55.71 | 2:56 |
| R1901-11/PEG (0.62 μm) | 63 | 45.24 | 2:11 |
| R1901-11/SPAN (0.74 μm) | 72 | 51.43 | 2:40 |
| PAN-1 (0.613 μm) | 45 | 32.14 | 1:08 |
| PAN-2 (0.531 μm) | 52 | 37.14 | 1:32 |
| PAN-3 (0.367 μm) | 100 | 71.43 | 1:20 |
| Isopore Polycarbonate filter (0.40 μm) | 50 | 35.71 | 2:41 |
| MF-Millipore Type HAWP (0.45 μm) | 40 | 28.57 | 2:35 |

Example 9

Effect of Various Extractants on Recovery of Bacteria from Spiked Water Samples by Filtration Followed by Elution

*E. coli* was grown over night in TSB at 37° C. The culture was diluted to obtain approximately 100 cfu/ml and 1 ml of the solution was added to 1000 ml of sterile water to obtain approximately 100 cfu. A 47 mm membrane was cut from sheets or discs and placed on a vacuum filtration apparatus. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 5 ml of various extractants and vortexed (Fixed Speed Vortex Mixer, VWR, West Chester, Pa.) at room temperature for 1 to 2 minutes. The solution was plated on 3M PETRIFILM *E. coli*/Coliform Count Plates according to manufacturer's instruction and incubated overnight at 37° C. The plates were read using 3M PETRIFILM Plate Reader and colony forming units (cfu) were determined. The results obtained are shown below in Table 6. Use of 0.2% Tween-20 and phosphate buffered saline (PBS, Invitrogen, Carlsbad, Calif.) showed better recovery than Triton-X-100 (Sigma-Aldrich Co., St. Louis, Mo.) or water. With Tween-20, the recovery ranged from 35% to 77%, while with PBS it was 33% to 79%. With sterile MILLI-Q water (Millipore Corp., Billerica, Mass.) and Trition-X-100 the recoveries were only 11% to 46%.

TABLE 6

Recovery of E. coli by filtration and elution using various extractants from membranes

| Membranes | 0.2% Tween-20 | 0.1% Triton-X-100 | PBS | Milli-Q Water |
|---|---|---|---|---|
| R1933-7/SPAN (0.34 μm) | 76.7% | 37.1% | 73.8% | 26.2% |
| R1901-8B/SPAN (0.49 μm) | 65.2% | 31.4% | 69.0% | 35.7% |
| PAN-3 (0.367 μm) | 63.5% | 46.2% | 78.6% | 35.7% |
| Isopore Polycarbonate (0.40 μm) | 34.7% | 10.7% | 33.3% | 19.0% |

Example 10

Effect of Tween-20 Concentrations on Recovery of Bacteria

E. coli was grown over night in TSB at 37° C. The culture was diluted to obtain approximately 100 cfu/ml and 1 ml of the solution was added to 1000 ml of sterile water to obtain approximately 100 cfu. A 47 mm membrane was cut from sheets or discs and placed on a vacuum filtration apparatus. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 5 ml of various concentrations of Tween-20 and vortexed (Fixed Speed Vortex Mixer, VWR, West Chester, Pa.) at room temperature for 1 to 2 minutes. The solution was plated on 3M PETRIFILM E. coli/Coliform Count Plates according to manufacturer's instruction and incubated overnight at 37° C. The plates were read using 3M PETRIFILM Plate Reader and colony forming units (cfu) were determined. The results obtained are shown below in Table 7. Use of 0.1% or 0.2% Tween-20 gave the best recoveries from all of the membranes tested.

TABLE 7

Effect of Tween-20 concentration on percent Recovery of E. coli by filtration and elution from membranes

| Membranes | Tween-20 concentration | | | | |
|---|---|---|---|---|---|
| | 0.01% | 0.05% | 0.10% | 0.20% | 0.50% |
| R1933-7/PEG (0.34 μm) | 57.5 | 45.7 | 51.6 | 70.8 | 20.6 |
| R1933-7/SPAN (0.34 μm) | 64.9 | 57.5 | 59.0 | 78.2 | 73.7 |
| R1901-8B/PEG (0.51 μm) | 38.3 | 47.2 | 63.4 | 67.8 | 23.6 |
| PAN-3 (0.367 μm) | 38.5 | 44.9 | 57.7 | 64.1 | 32.1 |
| Isopore Polycarbonate filter (0.40 μm) | 12.8 | 19.2 | 32.1 | 38.5 | 19.2 |
| MF-Millipore Type HAWP (0.45 μm) | 19.2 | 32.1 | 38.5 | 32.1 | 25.6 |

Example 11

Effect of Various Methods for Recovery of Bacteria from Membranes

E. coli was grown over night in TSB at 37° C. The culture was diluted to obtain approximately 100 cfu/ml and 1 ml of the solution was added to 1000 ml of sterile water to obtain approximately 100 cfu. A 47 mm membrane was cut from sheets or discs and placed on a vacuum filtration apparatus. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 5 ml of 0.2% Tween-20. The tubes were sonicated for 5 minutes using an ultrasonicator (Branson 2200, Branson Ultrasonics, Dansbury, Conn.), vortexed for 1 to 2 minutes (Fixed Speed Vortex Mixer, VWR, West Chester, Pa.) or shaken in an orbital shaker (Newbrunswik Scientific shaker, Model Innova 4000) for 10 minutes at room temperature. The solutions were plated on 3M PETRIFILM E. coli/Coliform Count Plates according to manufacturer's instruction and incubated overnight at 37° C. The plates were read using 3M PETRIFILM Plate Reader and colony forming units (cfu) were determined. The results obtained are shown below in Table 8.

TABLE 8

Recovery of E. coli from membranes after filtration by various methods of extraction

| | Sonication | | Vortexing | | Shaking | |
|---|---|---|---|---|---|---|
| | Total cfu recovered | % recovery | Total cfu recovered | % recovery | Total cfu recovered | % recovery |
| Input cells | 96 cfu | | | | | |
| R1933-7/PEG (0.34 μm) | 28 | 29.5 | 63 | 66 | 12 | 12.5 |
| R1901-8B/PEG (0.51 μm) | 30 | 31.3 | 75 | 78.1 | 15 | 15.6 |
| PAN-3 (0.367 μm) | 32 | 33.0 | 47 | 48.6 | 32 | 33.3 |
| Isopore polycarbonate filter (0.40 μm) | 22 | 22.6 | 42 | 43.4 | 15 | 15.6 |
| MF-Millipore Type HAWP (0.45 μm) | 28 | 29.5 | 38 | 39.9 | 10 | 10.4 |

Example 12

Recovery of Bacteria from Membranes Using Foam Elution

*E. coli* was grown over night in TSB at 37° C. The culture was diluted to obtain approximately 100 cfu/ml and 1 ml of the solution was added to 50 ml of sterile water to obtain approximately 100 cfu. A 25 mm membrane was cut from sheets or discs and placed in a 25 mm Swinnex filter holder (Millipore Corp., Billerica, Mass.). The filter holder was attached to a vacuum manifold (Waters Corporation, Milford, Mass.) and a 50 ml syringe was attached to the other end of filter holder. The spiked water sample was filtered through the various membranes at vacuum pressure of about 20 inches of mercury using an AIR CADET Vacuum/Pressure Station. The filter holder with the membrane was attached to HSC 40 bench-top concentrator (InnovaPrep, Drexel, Mo.). The system generates foam of the extractant solution and the bacteria were eluted by passing the foam (1 ml of 0.05% Tween-20) through the membrane.

The extracted solutions were plated on 3M PETRIFILM *E. coli*/Coliform Count Plates according to manufacturer's instruction and incubated overnight at 37° C. The plates were read using 3M PETRIFILM Plate Reader and colony forming units (cfu) were determined. The results obtained are shown below in Table 9. The foam elution method offers an advantage for eluting biological organisms in small volumes and enables easy extraction of nucleic acids without further concentration of eluted material.

TABLE 9

Recovery of *E. coli* from membranes after filtration by foam elution

|  | Total cfu in 1 ml | % Recovery |
|---|---|---|
| Input | 86 cfu |  |
| R1933-7/SPAN (0.34 μm) | 46 | 53.5 |
| R1933-7/PEG (0.34 μm) | 49 | 57.0 |
| PAN-3 (0.367 μm) | 47 | 54.7 |
| Isopore polycarbonate filter (0.40 μm) | 35 | 40.7 |
| MF-Millipore Type HAWP (0.45 μm) | 25 | 29.1 |

Example 13

Recovery of Bacteria from Spiked Water Samples Followed by Growth

*E. coli*, *Salmonella enterica* subsp. *enterica*, and *Enterococcus faecalis* were grown over night in TSB at 37° C. The culture was diluted to obtain approximately 10 cfu/ml and 1 ml of the solution was added to 1000 ml of sterile water to obtain approximately 10 cfu. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 10 ml of Terrific Broth (TB) or tryptic soy broth (TSB) and agitated at 300 rpm in a Newbrunswik Scientific shaker, Model Innova 4000 for 2 hours at 37° C. Control tubes were set up by spiking about 10 cfu (100 μl of $10^2$ cfu/ml) into 10 ml TB and were grown similarly. At the end of two hours, growth media from the tubes were plated on 3M PETRIFILM *E. coli*/Coliform Count Plates (for *E. coli*) and Aerobic Count Plates (for *S. enterica* and *Enterococcus faecalis*) and incubated overnight at 37° C. The plates were read using 3M PETRIFILM Plate Reader and colony forming units (cfu) were determined. The input number of cells was used to calculate the fold-increase.

TABLE 10

Increase in cell number of *E. coli* after filtration and growth in TB for two hours

|  | Total cfu in 5 ml | Fold-increase | Total cfu in 5 ml | Fold-increase |
|---|---|---|---|---|
| Input to 1 liter water | 6 cfu |  | 24 cfu |  |
| Control (no filtration) | 65 | 10.83 | 250 | 10.42 |
| R1901-11/SPAN (0.74 μm) | 68 | 11.33 | 195 | 8.13 |
| PAN-3 (0.367 μm) | 67 | 11.17 | 225 | 9.38 |
| Isopore polycarbonate filter (0.40 μm) | 43 | 7.17 | 105 | 4.38 |

TABLE 11

Increase in cell number of *E. coli* after filtration and growth in TB for two hours

|  | Total cfu in 10 ml | Fold-increase |
|---|---|---|
| Input to I liter water | 11 cfu |  |
| Control (no filtration) | 150 | 13.64 |
| PAN-1 (0.613 μm) | 70 | 6.36 |
| PAN-2 (0.531 μm) | 100 | 9.09 |
| PAN-3 (0.367 μm) | 160 | 14.55 |
| R1901-8B/SPAN (0.49 μm) | 140 | 12.73 |
| R1901-11/SPAN (0.74 μm) | 110 | 10.00 |
| Isopore polycarbonate filter (0.40 μm) | 60 | 5.45 |
| MF-Millipore Type HAWP (0.45 μm) | 40 | 3.64 |

TABLE 12

Increase in *E. coli* cell numbers after filtration and growth in TB for two hours

|  | Total cfu in 10 ml | Fold-Increase |
|---|---|---|
| Input | 11 cfu |  |
| Control | 150 | 13.6 |
| R1933-18/SPAN (0.2 μm) | 120 | 10.9 |
| R1933-7/PEG (0.34 μm) | 130 | 11.8 |
| R1933-7/SPAN (0.34 μm) | 120 | 10.9 |
| R1901-8B/PEG (0.51 μm) | 110 | 10.0 |
| R1901-8B/SPAN (0.49 μm) | 140 | 12.7 |
| R1901-11/PEG (0.62 μm) | 90 | 8.2 |
| R1901-11/SPAN (0.74 μm) | 100 | 9.1 |
| PAN-3 (0.367 μm) | 107 | 9.7 |
| Isopore Polycarbonate filter (0.40 μm) | 70 | 6.4 |
| MF-Millipore Type HAWP (0.45 μm) | 60 | 5.5 |

TABLE 13

Increase in *E. coli* cell numbers after filtration and growth in TSB for two hours

|  | Total cfu in 10 ml | Fold-increase | Total cfu in 10 ml | Fold-increase |
|---|---|---|---|---|
| Input | 11 cfu |  | 44 cfu |  |
| Control | 150 | 13.6 | 540 | 12.3 |
| R1901-8B/SPAN (0.49 μm) | 145 | 13.2 | 350 | 8.0 |
| PAN-3 (0.367 um) | 130 | 11.8 | 310 | 7.0 |
| Isopore Polycarbonate filter (0.40 μm) | 85 | 7.7 | 230 | 5.2 |

TABLE 13-continued

Increase in *E. coli* cell numbers after filtration and growth in TSB for two hours

|  | Total cfu in 10 ml | Fold-increase | Total cfu in 10 ml | Fold-increase |
|---|---|---|---|---|
| MF-Millipore Type HAWP (0.45 μm) | 70 | 6.4 | 250 | 5.7 |

TABLE 14

Increase in *S. enterica* cell numbers after filtration and growth in TSB for two hours

|  | Total cfu in 10 ml | Fold-increase | Total cfu in 10 ml | Fold-increase |
|---|---|---|---|---|
| Input | 9 cfu |  | 36 cfu |  |
| Control | 40 | 4.4 | 150 | 4.2 |
| R1901-8B/SPAN (0.49 μm) | 35 | 3.9 | 130 | 3.6 |
| PAN-3 (0.367 um) | 30 | 3.3 | 150 | 4.2 |
| Isopore Polycarbonate filter (0.40 μm) | 22 | 2.4 | 90 | 2.5 |
| MF-Millipore Type HAWP (0.45 μm) | 25 | 2.8 | 110 | 3.1 |

TABLE 15

Increase in *E. coli* and *Enterococcus faecalis* cell numbers after filtration and growth in TSB for two hours

|  | *E. coli* | | *Enterococcus faecalis* | |
|---|---|---|---|---|
|  | Total cfu in 10 ml | Fold-increase | Total cfu in 10 ml | Fold-increase |
| Input | 13 cfu |  | 30 cfu |  |
| Control | 130 | 10.0 | 220 | 7.4 |
| R1933-7/PEG (0.34 μm) | 110 | 8.5 | 160 | 5.2 |
| R1933-7/SPAN (0.34 μm) | 120 | 9.2 | 180 | 6.0 |
| Isopore Polycarbonate filter (0.40 μm) | 70 | 5.4 | 130 | 4.2 |
| MF-Millipore Type HAWP (0.45 μm) | 50 | 3.8 | 60 | 2.0 |

Example 14

Recovery of Coliform Bacteria from Spiked Water Samples Followed by Growth

*E. coli*, *Enterobacter aerogenes*, *Enterobacter cloacae*, *Citrobacter freundii*, and *Citrobacter braakii* were grown over night in TSB at 37° C. The culture was diluted to obtain approximately 100 cfu/ml and 0.4 ml of the solution was added to 1000 ml of sterile water to obtain approximately 40 cfu. The solution was filtered through the various membranes at vacuum pressure of about 20 inches of mercury using an AIR CADET Vacuum/Pressure Station. The membranes were removed aseptically and added to a sterile polystyrene 50-ml centrifuge tube (BD Biosciences, San Jose, Calif.) with 10 ml of Terrific Broth (TB, Sigma-Aldrich Co., St. Louis, Mo.) or tryptic soy broth (TSB, BD Biosciences, San Jose, Calif.) and agitated at 300 rpm in a Newbrunswik Scientific shaker, Model Innova 4000 for 2.5 or 3 hours at 37° C. Control tubes were set up by spiking about 40 cfu (400 μl of 100 cfu/ml) into 10 ml TB and were grown similarly. At the end of incubation period, growth media from the tubes were plated on 3M PETRIFILM *E. coli*/Coliform Count Plates and incubated overnight at 37° C. The plates were read using 3M PETRIFILM Plate Reader and colony forming units (cfu) were determined. The input number of cells was used to calculate the fold-increase.

TABLE 16

Increase in cell number of coliform bacteria after filtration and growth in TB for two and half hours

|  | Total cfu in 10 ml | Fold-Increase |
|---|---|---|
| *E. coli* |  |  |
| Input | 92 cfu |  |
| Control | 2500 | 27.2 |
| R1933-7/PEG (0.34 μm) | 1900 | 20.7 |
| Isopore Polycarbonate filter (0.40 μm) | 820 | 8.9 |
| MF-Millipore Type HAWP (0.45 μm) | 530 | 5.8 |
| *Enterobacter aerogenes* |  |  |
| Input | 80 cfu |  |
| Control | 2450 | 30.6 |
| R1933-7/PEG (0.34 μm) | 1500 | 18.8 |
| Isopore Polycarbonate filter (0.40 μm) | 900 | 11.3 |
| MF-Millipore Type HAWP (0.45 μm) | 450 | 5.6 |
| *Enterobacter cloacae* |  |  |
| Input | 52 cfu |  |
| Control | 1100 | 21.2 |
| R1933-7/PEG (0.34 μm) | 550 | 10.6 |
| Isopore Polycarbonate filter (0.40 μm) | 310 | 6.0 |
| MF-Millipore Type HAWP (0.45 μm) | 170 | 3.3 |
| *Citrobacter braakii* |  |  |
| Input | 10 cfu |  |
| Control | 150 | 15 |
| R1933-7/PEG (0.34 μm) | 100 | 10 |
| Isopore Polycarbonate filter (0.40 μm) | 60 | 6 |
| MF-Millipore Type HAWP (0.45 μm) | 40 | 4 |
| *Citrobacter freundii* |  |  |
| Input | 80 cfu |  |
| Control | 900 | 11.3 |
| R1933-7/PEG (0.34 μm) | 650 | 8.1 |
| Isopore Polycarbonate filter (0.40 μm) | 400 | 5.0 |
| MF-Millipore Type HAWP (0.45 μm) | 250 | 3.1 |

TABLE 17

Increase in cell number of coliform bacteria after filtration and growth in TSB for three hours

|  | Total cfu in 10 ml | Fold-Increase |
|---|---|---|
| *E. coli* |  |  |
| Input | 88 cfu |  |
| Control | 5100 | 58.0 |
| R1933-7/PEG (0.34 μm) | 6000 | 68.2 |
| Isopore Polycarbonate filter (0.40 μm) | 3500 | 39.8 |
| MF-Millipore Type HAWP (0.45 μm) | 2800 | 31.8 |
| *Enterobacter aerogenes* |  |  |
| Input | 76 cfu |  |
| Control | 4900 | 64.5 |
| R1933-7/PEG (0.34 μm) | 4000 | 52.6 |
| Isopore Polycarbonate filter (0.40 μm) | 2850 | 37.5 |
| MF-Millipore Type HAWP (0.45 μm) | 2200 | 28.9 |
| *Citrobacter freundii* |  |  |
| Input | 68 cfu |  |
| Control | 2050 | 30.1 |
| R1933-7/PEG (0.34 μm) | 1400 | 20.6 |

TABLE 17-continued

Increase in cell number of coliform bacteria after filtration and growth in TSB for three hours

| | Total cfu in 10 ml | Fold-Increase |
|---|---|---|
| Isopore Polycarbonate filter (0.40 μm) | 700 | 10.3 |
| MF-Millipore Type HAWP (0.45 μm) | 875 | 12.9 |

Example 15

Development of Primers and Probes for Detection of E. coli by PCR

Two *E. coli* genes uidA (coding for b-glucoronidase) and tufA (coding for protein chain elongation factor EF-Tu) were selected as target genes. PCR primers and probes were designed based on alignment of all the sequences available in GenBank. The primers designed were:

```
uidA:
                                        (SEQ ID NO: 1)
Forward primer 5'-TCTACTTTACTGGCTTTGGTCG-3'

(SEQ ID NO: 2)
Reverse primer 5'-CGTAAGGGTAATGCGAGGTAC-3'

(SEQ ID NO: 3)
Probe 5'-6-FAM-AGGATTCGATAACGTGCTGATGGTGC-
3'-Iowablack FQ tufA:
                                        (SEQ ID NO: 4)
Forward primer: 5'-TCACCATCAACACTTCTCACG-3'

(SEQ ID NO: 5)
Reverse primer: 5'-CAGCAACTACCAGGATCGC-3'

(SEQ ID NO: 6)
Probe: 5'-6-FAM-TGAATACGACACCCCGACCCG-3'-
Iowablack FQ
```

The primers and probes were synthesized by IDT DNA Technologies, Coralville, Iowa. Designed primers were used at 250 to 500 nM and probe at 125 to 250 nM with 10 μl 2× TaqMan Fast Universal Master Mix (Applied Biosystems, Foster City, Calif.) and 5 μl of DNA template. In addition, commercially available reagents for detection of *E. coli* from Primer Design Ltd, Southampton, UK (Quantification of *E. coli* standard kit) and BioGx, Birmingham, Ala. (*E. coli* species Scorpions) were used according to manufacturer's instructions.

*E. coli* cells were diluted serially in Butterfield phosphate buffer and DNA template was prepared by mixing 100 μl of PREPMAN Ultra sample prep reagent (Applied Biosystems) with 25 μl of bacterial dilutions and boiling for 10 minutes. The boiled suspension was cooled, spun at 14,000 RPM for 2 minutes and supernatant was transferred to a clean tube. 5 μl of DNA sample was added to 96-well PCR plate containing 20 μl of reaction mix (primers, probes, and enzyme mix). Thermal cycling was carried out using ABI 7500 sequence detection system with the following conditions: 2 minutes at 95° C. for denaturation followed by 40 cycles of: 20 seconds at 95° C. and 1 minute at 60° C. As shown below the limit of detection with the PCR was about 100 cfu.

TABLE 18

PCR detection of *E. coli*

| Approximate Concentration of bacteria in PCR tube | In-House reagents Ct | | Primer Design Kit Ct | BioGX kit Ct |
|---|---|---|---|---|
| | uidA | tufA | uidA | |
| NTC | 40 | 40 | 40 | 40 |
| 1 cfu | 40 | 40 | 40 | 40 |
| 10 cfu | 38.34 | 39.37 | 38.8 | 39.1 |
| 100 cfu | 34.94 | 35.42 | 33.4 | 33.7 |
| 1000 cfu | 30.96 | 30.33 | 29.8 | 29.5 |
| 10000 cfu | 27.04 | 25.83 | 24.3 | 23.4 |
| 100000 cfu | 22.25 | 22.86 | 20.3 | 20.7 |

Example 16

Detection of Bacteria from Spiked Water Samples by PCR

*E. coli* was grown over night in TSB at 37° C. The culture was diluted to obtain approximately 10 cfu/ml and 1 ml of the solution was added to 1000 ml of sterile water to obtain approximately 10 cfu. This solution was filtered through various membranes at vacuum pressure of about 20 inches of mercury using an AIR CADET Vacuum/Pressure Station. The membranes were removed aseptically and added to a 50-ml tube with 10 ml of TB (Sigma-Aldrich Co., St. Louis, Mo.) and agitated at 300 rpm in a Newbrunswik Scientific shaker, Model Innova 4000 for two hours at 37° C. Control tubes were set up by spiking about 10 cfu (100 μl of $10^2$ cfu/ml) into 10 ml TB and were grown similarly. All the samples were set up in duplicates. At the end of two hours, growth media from one set of tubes were plated on 3M PETRIFILM *E. coli*/Coliform Count Plates and incubated overnight at 37° C. The plates were read using 3M PETRIFILM Plate Reader and colony forming units (cfu) were determined.

From the other set of tubes, the growth media containing cells were spun at 5000 rpm for 20 minutes to pellet cells. DNA was extracted using Qiagen Mini DNA extraction kit according to manufacturer's instructions and DNA was eluted in 10 μl. 5 μl of extracted DNA was added to 20 μl PCR assay mix and PCR was carried out as described above with primer and probes for uidA gene (Primer Design kit). The entire process from filtration followed by growth and detection by PCT took about 4 hours.

As shown below, the fold-increase varied from 5-fold to 18-fold. From 1000 ml water samples spiked with 10 cfu of *E. coli*, the modified TIPS membranes showed 9- to 18-fold increase and were positive by PCR. The commercial membranes showed only 5- to 6-fold increase and did not show any amplification of target DNA.

TABLE 19

Rapid Detection of *E. coli* by PCR

| | Total cfu in 10 ml | Fold-increase | PCR Assay (Ct) | Amplification |
|---|---|---|---|---|
| Input to 1000 ml water | 10 cfu | | | |
| NTC | | | 40 | No |
| Control (no filtration) | 156 | 15.6 | 32.1 | Yes |
| R1933-7/PEG (0.34 mm) | 150 | 15.0 | 32.7 | Yes |
| R1933-7/SPAN (0.34 mm) | 175 | 17.5 | 31.9 | Yes |
| R1901-8B/PEG (0.51 mm) | 98 | 9.8 | 34.2 | Yes |
| R1901-8B/SPAN (0.49 mm) | 122 | 12.2 | 33.1 | Yes |

TABLE 19-continued

Rapid Detection of *E. coli* by PCR

| | Total cfu in 10 ml | Fold-increase | PCR Assay (Ct) | Amplification |
|---|---|---|---|---|
| R1901-11/PEG (0.62 mm) | 90 | 9.0 | 34.9 | Yes |
| R1901-11/SPAN (0.74 mm) | 102 | 10.2 | 34 | Yes |
| PAN-3 (0.367 mm) | 115 | 11.5 | 33 | Yes |
| Isopore Polycarbonate (0.40 mm) | 60 | 6.0 | 38.8 | No |
| MF-Millipore Type HAWP (0.45 mm) | 50 | 5.0 | 39 | No |

Example 17

Preparation and Evaluation of Bags with Polypropylene Membranes

A 4 wt % (weight %) surfactant solution was prepared by dissolving sorbitol monolaurate (SPAN 20 available from Croda, New Castle Del.) in 2-propanol (Alfa Aesar, Ward Hill, Mass.). R1930-10, R1901-11, and R1901-8B membranes (Table 1) were separately placed in polyethylene (PE) bags with sufficient surfactant solution to saturate them. The membranes saturated immediately. Excess surfactant solution was removed by rubbing the bags to squeeze the solution out of the bag. The membranes were removed from the bags and air dried at room temperature. The properties for the treated and untreated membranes were characterized for the properties shown in Table 2. The Tight Zone Thickness refers to the approximate thickness of the layer having the smaller pore size. The dried membranes were stored in a plastic bag until used.

Figure 11:
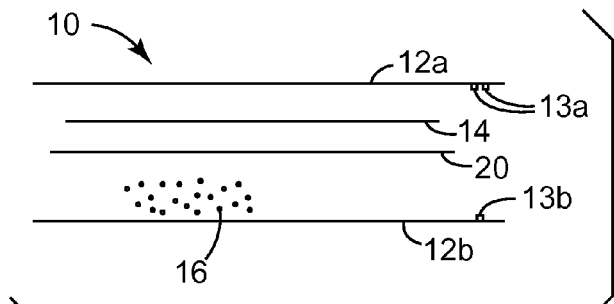
FIG. 11. An exploded side view of one embodiment of a filtration device according to the present disclosure.
Figure 12:
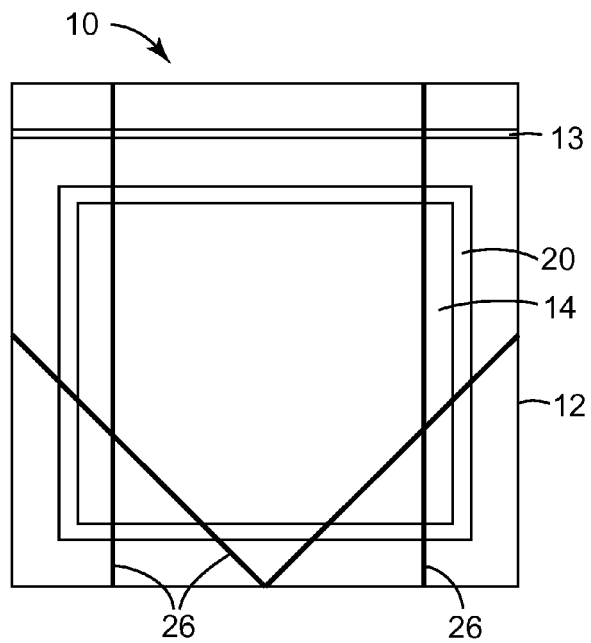
FIG. 12. A plan view of the assembled filtration device of FIG. 11.

The membranes were constructed as a bag concentration device similar to the device shown in FIGS. 11 and 12. Bags including each membrane were constructed in the same manner. An 8 inch by 8 inch ZIPLOC polyethylene bag (S.C. Johnson & Son, Inc., Racine, Wis.) was cut along the sealed edges and separated into two pieces. A single layer of dry membrane was cut into a pentagonal shape having three square five-inch sides and two equilateral sides of about 2.7 inches. The membrane was stacked atop a polypropylene nonwoven sheet (TYPAR, Reemay Inc, Charleston, S.C.) having the same dimensions with the open side of the multizone membrane facing the nonwoven sheet. The stack was then placed on the inner surface of one piece of the ZIPLOC bag with the square shape facing the ZIPLOC seal and the triangle forming a v-shape near the bottom of the bag, and the tight side of the membrane facing the inner surface of the bag. FIG. 11 shows an exploded view of the bag concentration device 10 with the following components: ZIPLOK bag sheets (container components 12a and 12b with interlocking closure components 13a and 13b), polypropylene nonwoven sheet (nonwoven backing 20), filter membrane 14, and superabsorbent particles (absorbent member 16). Four edges of the membrane and nonwoven pentagon were heat sealed to the ZIPLOC bag to form a pouch with the five-inch side of the pentagon facing the ZIPLOC seal at the top of the bag left open, as shown in FIG. 12. The two sides of the ZIPLOC bag were then heat sealed (seals 26) so the nonwoven faced the opposing wall of the bag to form a concentration bag similar to the one shown in FIG. 8.

Each bag was evaluated by placing 3.8 g of superabsorbent hydro gel particles (polyacrylate-polyalcohol) into each bag outside of the pouch. For each test, a broth was prepared by adding 1.125 ml of an ethylene oxide/propylene oxide surfactant PLURONIC L64 (PL64, available from BASF, Mount Olive, N.J.) and 0.45 g of bovine serum albumin (BSA, Sigma-Aldrich Co., St. Louis, Mo.) were added to 225 ml of sterilized tryptic soy broth (TSB) obtained as Quick-Enrich TSB (3M Co., St. Paul, Minn.) to final concentrations of 0.5% PL64 and 0.2% BSA. The broth was then inoculated with 225 µl of Butterfield phosphate buffer containing approximately $10^5$ cfu (colony forming units)/ml of *Listeria innocua* (ATCC 33090). The bacterial broth was then poured into the pouch of the concentration bag (the tight side of the membrane) and propped upright on a bench at room temperature until about three ml of the solution remained in the pouch (20-30 minutes) and the absorption time was recorded. The remaining liquid was removed with a pipette and transferred to a 15 ml graduated centrifuge tube to measure the volume. Each concentrated sample was then diluted 10-fold with Butterfield's buffer and 100 µl of the dilution was plated on a Modified Oxford Medium plate (MOX plate obtained from Hardy Diagnostics, Santa Maria, Calif.) and incubated at 37° C. for 24 hours.

The control represents the initial concentration. Control samples were prepared in the same manner as the evaluation assays but not concentrated. Separate controls were tested with each set of membranes, e.g., Control 1 was tested at the same time as the SPAN 20 treated membranes and Control 2 was tested at the same time as the PEG treated membranes.

Each evaluation was replicated a second time and the Bacteria Concentration represents two different separate counts after concentrating. The concentration factor is the final concentration divided by the initial concentration of bacteria. Test results for the SPAN 20 treated membranes are shown in Table 20.

TABLE 20

Bacterial Recovery Rates and Absorption Times for TIPS Membranes

| Membrane | Bacteria concentration (cfu/ml) | Volume recovered (ml) | Recovered Bacteria numbers | Recovery rate | Concentration factor | Absorption time (min) |
|---|---|---|---|---|---|---|
| R1930-10 | 6850 | 3 | $2.06 \times 10^4$ | 58.9% | 44 | 36 |
| SPAN 20 | 5700 | 3.8 | $2.17 \times 10^4$ | 62.1% | 37 | 36 |

TABLE 20-continued

Bacterial Recovery Rates and Absorption Times for TIPS Membranes

| Membrane | Bacteria concentration (cfu/ml) | Volume recovered (ml) | Recovered Bacteria numbers | Recovery rate | Concentration factor | Absorption time (min) |
|---|---|---|---|---|---|---|
| R1901-11 | 9550 | 3 | $2.87 \times 10^4$ | 82.2% | 62 | 22 |
| SPAN 20 | 7550 | 2.8 | $2.11 \times 10^4$ | 60.6% | 49 | 22 |
| R1901-8B | 7850 | 3 | $2.36 \times 10^4$ | 67.5% | 51 | 20 |
| SPAN 20 | 7900 | 3 | $2.37 \times 10^4$ | 68.0% | 51 | 20 |
| Control 1 | 155 | 225 | $3.49 \times 10^4$ | — | — | — |
| R1901-8B | 4250 | 23.4 | $1.45 \times 10^4$ | 75.6% | 50 | 25 |
| PEG | 4050 | 3.2 | $1.30 \times 10^4$ | 67.8% | 48 | 25 |
| Control 2 | 69 | 225 | $1.55 \times 10^4$ | — | — | — |

Example 18

Preparation and Evaluation of Bags with Polypropylene Membranes

A 5 wt % stock solution of ethylene vinyl alcohol copolymer was prepared by dissolving an ethylene-vinyl alcohol copolymer (EVAL44) having 44 mole % ethylene content (44% ethylene content poly(vinylalcohol co-ethylene polymer) obtained under the product number 414107 from Sigma-Aldrich Co., St. Louis, Mo.) in an ethanol (AAPER Alcohol and Chemical Co. Shelbyville, Ky.)/water solvent mixture (70 vol % ethanol) in a water bath at temperature 70-80° C.

From the above stock solution, a polyethylene glycol (PEG) coating solution was made containing 1 wt % EVAL44, 2 wt % polyethylene glycol (600) diacrylate (obtained under product number SR610 from Sartomer, Warrington, Pa.), 1 wt % reactive photoinitiator VAZPIA (2-[4-(2-hydroxy-2-methylpropanoyl)phenoxy]ethyl-2-methyl-2-N-propenoylamino propanoate, as disclosed in U.S. Pat. No. 5,506,279) in ethanol/water mixture solvent (70 vol % ethanol).

Microporous membranes R1933-7 and R1933-18 (Table 1) were saturated with the PEG coating solution in a heavy weight PE bag, then removed from the bag. Excess solution was removed by wiping the surface of the saturated membrane with a paper towel. The membrane was air-dried at room temperature for 10-12 hours. The dry membrane was then saturated with a 20 wt % NaCl aqueous solution and excess solution was removed. The membrane was then placed on a conveyor belt of a UV curing system (Fusion UV system with H-bulb from Fusion UV Systems, Inc., Gaithersburg, Md.) and cured in an inert nitrogen atmosphere chamber. The belt speed was 20 feet per minute (fpm). The membrane was turned over and run through the UV system a second time at the same speed with the opposite membrane side facing the light source. The cured membrane was washed in excess deionized water and dried at 90° C. for 1 to 2 hours until completely dry. The dried membranes, with a permanent treatment, were stored in a PE bag at room temperature.

Bag concentration devices were prepared as described in Example 17.

Example 19

Preparation and Evaluation of Bags with Polyacrylonitrile Membranes

Various polyacrylonitrile (PAN) polymer membranes (PAN-1, PAN-2, PAN-3, PAN-4, and PAN-5) were made as disclosed in Korean Patent Application No. KR20040040692. A 10.5-wt % solution of polyacrylonitrile (MW. 150,000) polymer in N,N-dimethylacetamide (DMAC) was prepared by dispersing the polymer in the liquid. A constant flow of PAN polymer solution (50 ul/min/hole) was pumped to a syringe connected to a high voltage source. An electric force of 90-100 Kv was introduced to the syringe which caused ejection of the polymer solution into the air to form electrospun PAN nanofibers. The fibers were collected on a web to form a bulky batt. To reduce the bulkiness and increase the structural integrity of this electrospun PAN nanofibers, post-treatment was carried out by calendering at 140° C. and at pressures between about 10 to 20 kgf/cm³. No other subsequent treatments were used. The membranes were stored in PE bags at room temperature. The membranes had pore sizes of 0.2 μm, 0.53 μm, and 0.73 μm for the PAN-4, PAN-2, and PAN-5 membranes, respectively. Bag concentration devices were prepared as described in Example 17.

The bags were evaluated according to the same procedure as described in Example 17 except that 3.9 grams of hydrogel was used in each bag. Test results are shown in Table 21.

TABLE 21

Bacterial Recovery Rate for Polyacrylonitrile Membranes

| Membrane (pore size) | Bacteria concentration (cfu/ml) | Volume recovered (ml) | Recovered Bacteria numbers | Recovery rate | Concentration factor | Absorption time (min) |
|---|---|---|---|---|---|---|
| PAN-4 | 700 | 2.5 | $1.75 \times 10^3$ | 16.2% | 15 | 40 |
| (0.2 μm) | 500 | 3.5 | $1.75 \times 10^3$ | 16.2% | 10 | 40 |
| PAN-2 | 1850 | 3.7 | $6.85 \times 10^3$ | 63.4% | 36 | <10 |
| (0.5 μm) | 2250 | 3.4 | $6.85 \times 10^3$ | 50.0% | 47 | <10 |
| PAN-5 | 850 | 2.6 | $2.21 \times 10^3$ | 20.5% | 18 | <10 |
| (0.7 μm) | 1350 | 4.5 | $6.05 \times 10^3$ | 56.3% | 28 | <10 |
| Control | 48 | 225 | $1.08 \times 10^3$ | — | — | — |

Example 20

Preparation of Bags with Nylon Membranes

Nylon Membrane Liquid Filter product numbers 080ZN (0.8 μm) and 0606SN (0.6 μm) were obtained from 3M Purification Inc., Meriden, Conn.

Bag concentration devices were prepared as described in Example 17.

Example 21

Preparation of Bags with Polycarbonate Membranes 0.8 μm and 0.6 μm polycarbonate membrane filters were obtained from GE Osmonics (Hopkins, Minn.). Bag concentration devices were prepared as described in Example 17.

Example 22

Preparation of Bags with Polyether/Polysulfone (PES) Membranes 0.8 μm and 0.6 μm polyether/polysulfone (PES) membranes were obtained from GE Osmosics (Hopkins, Minn.). Bag concentration devices were prepared as described in Example 17.

Example 23

Evaluation of Membranes

Bags containing a 0.6 μm nylon membrane (Example 20) and bags containing a 0.8 μm polycarbonate membrane (Example 21) were evaluated according to the procedure described in Example 17 except that 4.0 grams of hydrogel was used in each bag. Bags containing the 0.6 μm nylon membrane also evaluated using a TSB broth prepared as described above, except that the surfactant used was 0.01% fluorosurfactant (3M NOVEC FC-4430, 3M Co., St. Paul, Minn.) instead of PLURONIC L64. Test results are shown in Table 22.

TABLE 22

Bacteria Recovery From Nylon and Polycarbonate Membranes

| Membrane (pore size) | Bacteria concentration (cfu/ml) | Volume recovered (ml) | Recovered Bacteria numbers | Recovery rate | Concentration factor | Absorption time (min) |
|---|---|---|---|---|---|---|
| Nylon | 1600 | 2.3 | $3.60 \times 10^3$ | 17.8% | 18 | 70 |
| (0.6 μm) | 1600 | 1.4 | $2.24 \times 10^3$ | 11.1% | 18 | 70 |
| Nylon (0.6 μm) 0.01% FC4430 | 3200 | 1.6 | $5.12 \times 10^3$ | 25.3% | 36 | 70 |
| Polycarbonate | 1500 | 2.7 | $4.05 \times 10^3$ | 20.0% | 17 | 90 |
| (0.8 μm) | 2500 | 1.3 | $3.25 \times 10^3$ | 16.1% | 28 | 90 |
| Control | 90 | 225 | $2.03 \times 10^4$ | | | |

Bags containing a 0.8 µm nylon membrane (Example 20) and bags containing a 0.8 µm PES membrane (Example 22) were evaluated according to the procedure described in Example 17 except as follows. The amount of hydrogel used in each bag was about 4.0 grams. The insides of the bags were sterilized by spraying the inside of the bag with isopropyl alcohol, propping the bag open, and irradiating the bag with ultraviolet light for 45 minutes. The tryptic soy broth contained 0.6% Yeast Extract prepared by dissolving 30 grams of TSB with 3 grams of Yeast Extract in 1 liter of deionized water. One of two surfactants, as indicated in Table 23 was added to the broth—0.2% (w/v) PLURONIC L64 and 0.2% Tween 80 (v/v) (Sigma-Aldrich Co., St. Louis, Mo.). The resulting broth (225 ml) was inoculated with 225 µl of Butterfield's Buffer containing about $1 \times 10^7$ cfu/ml of *Listeria innocua* (ATCC 33090) and mixed well. The broth was then poured into the pouch of the sample concentration bag and propped upright for 50-90 minutes. The concentrated sample was collected, measured, and diluted in Butterfield's buffer 10-fold sequentially in 3 ml. Then 1 ml of the $3^{rd}$ dilutions of each sample was plated on AC PETRIFILM Plates (3M, Co. St. Paul, Minn.). The plates were incubated at 37° C. for 24 hours and the colonies were counted. Table 23 shows the bacterial recovery results.

TABLE 23

Bacterial Recovery Rate for Polyether Sulfone and Nylon Membranes

| Membrane (Surfactant) | Bacteria concentration (cfu/ml) | Volume recovered (ml) | Recovered Bacteria numbers | Recovery rate | Concentration factor | Absorption time (min) |
|---|---|---|---|---|---|---|
| Nylon 0.8 µm (0.2% Tween 20) | 32000 | 6.5 | $2.08 \times 10^5$ | 26.0% | 9 | 60 |
| Nylon 0.8 µm (0.2% PL64) | 396500 | 7.4 | $2.92 \times 10^5$ | 36.6% | 11 | 60 |
| PES (0.2% Tween 20) | 29500 | 12.6 | $3.72 \times 10^5$ | 46.5% | 8 | 100 |
| PES (0.2% PL64) | 34500 | 3.0 | $1.04 \times 10^5$ | 18.22% | 10 | 100 |
| Control | 3550 | 225 | $7.99 \times 10^4$ | | | |

Example 24

Large Water Sample Collection System with Float Valve and Container

A large sample volume collection system was built using a four-gallon plastic carboy (P/N 073004, US Plastic Corporation, Lima Ohio). A 47 mm filter holder (Cat # EW-06623-22, Cole-Parmer Instrument Co., Vernon Hills, Ill.) was attached to a ½" float valve (Hudson Valve Company, Bakersfield, Calif.) using appropriate pipe fittings (Menards, Stillwater, Minn.). The float valve was fitted into the opening of the carboy so that the float will rise to stop water flow when the required amount was reached. To the other end of the filter holder appropriate pipe fittings were attached so that the filter holder can be attached to water source. A 47 mm membrane filter was placed in the filter holder and the device was attached to water source (tap). The water source was turned on and water was allowed to filter through the membrane. When the container was full (10 liters), the float valve shut of the water flow. The tap was turned off, the filter holder was detached, and the membrane filter was removed and processed for further analysis. The membrane was placed on blood agar (Hardy Diagnostics, Santa Maria, Calif.) or tryptic soy agar plate (Hardy Diagnostics) and the plate was incubated at 37° C. for 16 to 24 hours. The colony forming units were counted to determine levels of bacteria in 10 liters of water.

Example 25

Large Water Sample Collection System with Flow Meter

A large sample volume collection system was built by attaching a flow meter (Cat. # WU-05610-01, Cole-Parmer Instrument Co., Vernon Hills, Ill.) to a 47 mm filter holder (Cat # EW-06623-22, Cole-Parmer) using appropriate pipe fittings (Menards, Stillwater, Minn.). To the other end of the filter holder appropriate pipe fittings were attached so that the filter holder can be attached to water source. A 47 mm membrane filter was placed in the filter holder and the device was attached to water source (tap). The water source was turned on and water was allowed to filter through the membrane. The reading on the flow meter was used to determine the amount of water flowing through the filter and when the water flow reached the required amount (10 liters) the water flow was shut off manually. The filter holder was detached and the membrane filter was removed and processed for further analysis. The membrane was placed on blood agar (Hardy Diagnostics, Santa Maria, Calif.) or tryptic soy agar plate (Hardy Diagnostics) and the plate was incubated at 37° C. for 16 to 24 hours. The colony forming units were counted to determine levels of bacteria in 10 liters of water.

Example 26

Description of Process for Pipe Rehabilitation 1 to 10 liters of water sample is processed using preferred membrane filters. The retained bacteria can be eluted or grown further for detection by assays such as PCR, isothermal amplification, immunoassays, etc. The rapid detection will enable to determine presence or absence of bacteria in a short time (e.g., less than eight hours) allowing for faster to return service of restored pipes.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   providing a device that comprises:
   a pocket comprising a pocket surface that defines a pocket volume;
   an absorbent member disposed on at least a portion of the pocket surface; and
   a filter membrane disposed on at least a portion of the absorbent member in fluid communication with the pocket volume, wherein the filter membrane is in functional communication with the absorbent member, wherein the functional communication is capable of generating a water flux gradient sufficient to draw liquid across the filter membrane and into the absorbent member, wherein the absorbent member is enveloped by the filter membrane;
   passing a sample having a sample volume and comprising at least one biological organism through the filter membrane at a passive water volume flux of at least 10 L/m²·h·psi, wherein the filter membrane comprises a Bubble Point pore size of no more than 1.0 µm, thereby retaining at least one biological organism on a surface of the filter membrane; and
   detecting the at least one biological organism retained on the surface of the filter membrane;
   wherein passing the sample through the filter membrane comprises:
   adding the sample to the pocket volume; and
   permitting the absorbent member to absorb at least 50% of the sample volume.

2. The method of claim 1 wherein the passive water volume flux is at least 32 L/m²·h·psi.

3. The method of claim 1 wherein the passive water volume flux is at least 88 L/m²·h·psi.

4. The method of claim 1 wherein the Bubble Point pore size is no more than 0.8 µm.

5. The method of claim 1 wherein the Bubble Point pore size is no more than 0.2 µm.

6. The method of claim 1 wherein at least 30% of the biological organisms in the sample are retained on the surface of the filter membrane.

7. The method of claim 1 wherein at least 70% of the biological organisms in the sample are retained on the surface of the filter membrane.

8. The method of claim 1 wherein at least 90% of the biological organisms in the sample are retained on the surface of the filter membrane.

9. The method of claim 1 wherein at least 99% of the biological organisms in the sample are retained on the surface of the filter membrane.

10. The method of claim 1 wherein at least 99.5% of the biological organisms in the sample are retained on the surface of the filter membrane.

11. The method of claim 1 wherein the at least one biological organism is detected in situ on the surface of the filter membrane.

12. The method of claim 1 wherein detecting the at least one biological organism retained on the surface of the filter membrane comprises eluting the retained biological organism from the surface of the membrane prior to performing a detection assay.

13. The method of claim 12 wherein at least 50% of the retained biological organisms are eluted from the surface of the filter membrane.

14. The method of claim 13 wherein at least 90% of the retained biological organisms are eluted from the surface of the filter membrane.

15. The method of claim 1 wherein detecting the at least one biological organism comprises at least one of the following:
- contacting the biological organism with an antibody composition that specifically binds to the biological organism;
- detecting an enzyme activity of the biological organism;
- detecting a biological analyte of the biological organism;
- detecting a biological analyte produced by the biological organism, followed by detecting a portion of a nucleic acid from the biological organism;
- amplifying at least a portion of a nucleic acid molecule from the biological organism; and
- detecting the nucleotide sequence of the biological organism.

16. The method of claim 1 wherein the filter membrane comprises a polyolefin porous membrane, an ethylene-chlorotrifluoroethylene copolymer porous membrane, a polyacrylonitrile porous membrane, a polycarbonate porous membrane, a polyester porous membrane, a cellulose ester porous membrane, a polyamide porous membrane, a polyethersulfone porous membrane, a polysulfone porous membrane, a polyvinylidene fluoride (PVDF) porous membrane, a polyacrylonitrile nanofiber membrane, a PVDF nanofiber membrane, a cellulose ester nanofiber membrane, a polyvinyl acetate or alcohol nanofiber membrane, or a polyvinyl butyral nanofiber membrane.

17. The method of claim 1 wherein the filter membrane comprises a thermally-induced phase separation (TIPS) membrane or a nanofiber membrane.

18. The method of claim 1 wherein the at least one biological organism is detected no more than 24 hours after the sample is passed through the filter membrane.

19. The method of claim 18 wherein the at least one biological organism is detected no more than 12 hours after the sample is passed through the filter membrane.

20. The method of claim 19 wherein the at least one biological organism is detected no more than three hours after the sample is passed through the filter membrane.

21. The method of claim 1 wherein the sample comprises food.

22. The method of claim 1 wherein the sample comprises an environmental sample.

23. The method of claim 1 wherein the sample comprises a water sample.

24. The method of claim 1 further comprising performing an assay to quantify the detected biological organisms recovered from the surface of the filter membrane.

* * * * *